(12) United States Patent
Opdyke

(10) Patent No.: US 9,163,289 B2
(45) Date of Patent: Oct. 20, 2015

(54) KIT FOR DETECTING HIV-1 AND METHOD FOR DETECTING HIV-1 USING THE SAME

(75) Inventor: Jason Opdyke, Silver Spring, MD (US)

(73) Assignee: Hanwha Techwin Co., Ltd., Changwon-si (KR)

( * ) Notice: Subject to any disclaimer, the term of this patent is extended or adjusted under 35 U.S.C. 154(b) by 1099 days.

(21) Appl. No.: 13/161,121

(22) Filed: Jun. 15, 2011

(65) Prior Publication Data

US 2012/0052483 A1 Mar. 1, 2012

Related U.S. Application Data

(60) Provisional application No. 61/377,491, filed on Aug. 27, 2010.

(51) Int. Cl.
*C12Q 1/70* (2006.01)
*C12Q 1/68* (2006.01)

(52) U.S. Cl.
CPC ........................................ *C12Q 1/703* (2013.01)

(58) Field of Classification Search
None
See application file for complete search history.

(56) References Cited

U.S. PATENT DOCUMENTS

2002/0177131 A1* 11/2002 Fodor et al. ....................... 435/6

OTHER PUBLICATIONS

"Cy2, Cy3, Cy5 1D gel imaging using Cy dye lighting unit and epi RGB LED module" [online] May 2010 [retrieved on Jan. 25, 2015] retrieved from: http://www.syngene.com/assets/doc/Technical-notes/Cy-dye-gel-imaging-47.pdf.*
"Applied Biosystems Standard Dye Sets for Genotyping Applications" [online] Oct. 2005 [retrieved on Jan. 25, 2015] retrieved from: http://faculty.georgetown.edu/hamiltm1/DNA_Fragment_Sizing_Facility_files/ABI%20Dye%20Set%20card.pdf.*
"User manual: 4-Color Compensation Set for Check-Direct CPE" [online] Sep. 20, 2013 [retrieved on Jan. 25, 2015] retrieved from: http://check-points.com/downloads/manuals/4-Color_Compensation_Set_LC480_IFU_070-03_EN_20Sept2013.*
"Streptavidin-RED670TM Conjugate" [online] Sep. 13, 2001 [retrieved on Jan. 25, 2015] retrieved from: http://tools.lifetechnologies.com/content/sfs/manuals/19543024.pdf.*
"Lightning-Link® Rapid Texas Red® Conjugation Kit Data Sheet" [online] Jun. 24, 2014 [retrieved on Jan. 25, 2015] retrieved from: http://www.innovabiosciences.com/images/stories/innova/LL-Rapid%20Texas%20Red%20data%20sheet%20v1.pdf.*
"Real-Time PCR Systems Applied Biosystems 7900HT Fast Real-Time PCR System and 7300/7500 Real-Time PCR Systems Chemistry Guide" [online] May 2005 [retrieved on Jan. 25, 2015] retrieved from: http://www3.appliedbiosystems.com/cms/groups/mcb_marketing/documents/generaldocuments/cms_041440.pdf.*
"TYE™ 563" [online] [retrieved on Jan. 25, 2015] retrieved from: https://www.exiqon.com/ls/homeoflna/Chemistry/TYE%20563.pdf.*
"Biosearch Technologies Dye Selection, Handling, and Storage of BHQ Probes" [online] 2011 [retrieved on Jan. 25, 2015] retrieved from: http://www.biosearchtech.com/assets/bti_bhq_handling.pdf.*
"Iowa Black® Dark Quenchers" [online] [retrieved on Jan. 25, 2015] retrieved from: http://www.idtdna.com/site/Catalog/Modifications/Category/4.*
"HIV Life Cycle" [online] [retrieved on Jan. 26, 2015] retrieved from: http://www.aidsinfonetorg/uploaded/factsheets/8_eng_106.pdf.*
"Blood, Sweat, and Buffers: pH Regulation During Exercise" [online] [retrieved on Jan. 26, 2015] retrieved from: http://www.chemistry.wustl.edu/~edudev/LabTutorials/Buffer/Buffer.html.*

* cited by examiner

*Primary Examiner* — Samuel Woolwine
(74) *Attorney, Agent, or Firm* — Sughrue Mion, PLLC

(57) ABSTRACT

A method is described for the real-time detection of HIV-1 gene target DNA in a sample, including obtaining HIV-1 specific cDNA by reverse transcription, amplifying a portion of the cDNA, and detecting the amplicons so produced using probe labeled with a detectable marker.

11 Claims, 8 Drawing Sheets

KIT FOR DETECTING HIV-1 AND METHOD FOR DETECTING HIV-1 USING THE SAME

CROSS-REFERENCE TO RELATED APPLICATIONS

This application claims priority from U.S. Provisional Patent Application No. 61/377,491, filed on Aug. 27, 2010, the content of which is hereby incorporated by reference in its entirety.

FIELD

The disclosure describes a method for the real-time detection of HIV-1 in a test sample. Oligonucleotides suitable for use in the method are also disclosed.

BACKGROUND

Human immunodeficiency virus type-1 (HIV-1) causes acquired immunodeficiency syndrome (AIDS). AIDS is a serious and deadly disease, with over 33 million people infected worldwide. Everyday, about 7,000 people become infected with HIV, and about 6,000 people die of AIDS and AIDS-related illnesses. Since HIV, the pathogen that causes AIDS, was first isolated in the early 1980s, diverse research has been conducted regarding the treatment of AIDS around the world. However, researchers have not succeeded in developing an effective vaccine capable of preventing and treating AIDS.

There are two types of HIV: HIV-1 and HIV-2. Both types of HIV are transmitted by sexual contact, through blood, and from mother to child, and they appear to cause clinically indistinguishable AIDS. However, it seems that HIV-2 is less easily transmitted, and the period between initial infection and illness is longer in the case of HIV-2.

Worldwide, the predominant virus is HIV-1. The relatively uncommon HIV-2 type is concentrated in West Africa and is rarely found elsewhere. The strains of HIV-1 can be classified into four groups: the "major" group M, the "outlier" group O and two new groups, N and P. These four groups may represent four separate introductions of simian immunodeficiency virus into humans.

Group O appears to be restricted to west-central Africa and group N—a strain discovered in 1998 in Cameroon—is extremely rare. In 2009 a new strain closely relating to gorilla simian immunodeficiency virus was discovered in a Cameroonian woman. It was designated HIV-1 group P.1 More than 90% of HIV-1 infections belong to HIV-1 group M. Within group M there are known to be at least nine genetically distinct subtypes (or clades) of HIV-1. These are subtypes A, B, C, D, F, G, H, J and K.

Since the late 1990, various types of diagnostic kits to detect HIV have been developed. An immunological method using an antibody that recognizes a specific protein of HIV is one of the most widely used techniques for the diagnosis of HIV infection. These methods have reduced sensitivity when compared to nucleic acid testing assays. Methods for detecting HIV-1 have also been developed that use cultivated cells and nucleic acid probes. These methods require highly skilled professionals and are time consuming. In order to overcome these limitations, research into various diagnostic assays utilizing the polymerase chain reaction (PCR) has been conducted. In these methods, a specific portion of a nucleic acid sequence is amplified exponentially in a suitable reaction mixture containing at least DNA polymerase and template specific primers.

There remains an unmet need in the art to develop an accurate and reliable real-time method for detecting samples contaminated with HIV-1.

SUMMARY

According to an exemplary embodiment, a method for real-time detection of HIV-1 in a sample is provided.

In one embodiment, a method is described for a real-time detection of HIV-1 in a sample, including the steps of: providing a sample to be tested for the presence of HIV-1, extracting RNA from the sample; forming an amplification medium by mixing the RNA with a uracil-n-glycosylase, DNA polymerase, reverse transcriptase, appropriate deoxynucleoside triphosphates, a nucleic acid binding probe comprising a detectable marker with DNA and RNA nucleic acid sequences that are substantially complimentary to the HIV-1 target DNA, a reaction buffer, and an upstream primer and an downstream primer; thermally cycling the amplification medium between at least a denaturation temperature and an elongation temperature, wherein the upstream and downstream primers in combination amplify the target nucleic acid or a section thereof, wherein the section may be of any length provided that the section is unique to the HIV-1 genome under conditions where the nucleic acid sequences within the probe can form a RNA:DNA heteroduplex with the complimentary DNA sequences in the PCR fragment of the HIV-1 target DNA; forming a reaction mixture of a target nucleic acid sequence and a plurality of nucleic acid probes which each include a detectable marker under conditions wherein the first nucleic acid probe of the plurality of nucleic acid probes including a first detectable marker is allowed to hybridize to the target nucleic acid or a section thereof; utilizing secondary nucleic acid probes from the plurality of nucleic acid probes within the reaction mixture, wherein a plurality of activated detectable markers are formed; and detecting a real-time increase in the emission of a signal from the label on the probe, wherein the increase in signal indicates the presence of the HIV-1 target DNA in the sample.

In one aspect, the real-time increase in the emission of the signal from the label on the probe results from the RNase H cleavage of the heteroduplex formed between the probe and one of the strands of the PCR fragment.

In another embodiment, the method may be used to determine the quantity of the HIV-1 RNA in a sample.

The method further includes steps of: determining a threshold cycle number at which the intensity of the plurality of activated detectable markers reaches a fixed threshold value above a baseline value; and calculating the quantity of HIV-1 RNA in the sample by comparing the threshold cycle number determined for the target nucleic acid in the sample with the threshold cycle number determined for target nucleic acid of known amounts in standard solutions.

According to an exemplary embodiment, a kit is provided for the detection of HIV-1, containing a first primer, a second primer, and a probe, which allows a sensitive and accurate detection of HIV-1.

According to an embodiment, a kit for the real-time detection of HIV-1 is provided, having a first primer selected from the group consisting of SEQ ID NO: 1, SEQ ID NO: 2, SEQ ID NO: 3, SEQ ID NO: 4, SEQ ID NO: 5 and SEQ ID NO: 6.

According to an embodiment, a kit for the real-time detection of HIV-1 is provided, having a second primer selected from the group consisting of SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19.

According to an embodiment, a kit for the real-time detection of HIV-1 is provided, having a probe selected from the group consisting of SEQ ID NO: 22, SEQ ID NO: 23, SEQ ID NO: 24 and SEQ ID NO: 25.

In an embodiment, the kit may contain a first primer selected from the group consisting of SEQ ID NO: 7 and SEQ ID NO: 8.

In an embodiment, the kit may contain a second primer having the nucleotide sequence of SEQ ID NO: 9.

In an embodiment, the kit may contain a probe having the nucleotide sequence of SEQ ID NO: 20 and SEQ ID NO: 21.

In an embodiment, a first primer oligonucleotide includes an oligonucleotide of the sequence of SEQ ID NO: 26:
$X_1$AG$X_2$A$X_3$T$X_4$CA$X_5$ATGGCAGT$X_6$$X_7$T$X_8$AT$X_9$ CA$X_{10}$AATT (SEQ ID NO: 26), wherein $X_1$ is C or G $X_2$ is C or T, $X_3$ is G or T, $X_4$ is A or G, $X_5$ is A or G, $X_6$ is A or G or T, $X_7$ is T or C, $X_8$ is T or C, $X_9$ is T or C, and $X_{10}$ is T or C.

In an embodiment, a first primer oligonucleotide includes an oligonucleotide of the sequence of SEQ ID NO: 27:
CAGGA$X_1$TT$X_2$GGGATACC$X_3$TACAATCCTCAAA GTCAGGGAG$X_4$$X_5$GTAGA$X_6$T CCATGAAT (SEQ ID NO: 27), wherein $X_1$ is A or G, $X_2$ is C or T, $X_3$ is C or A, $X_4$ is C or T, $X_5$ is A or G, $X_6$ is A or G.

In an embodiment, a first primer oligonucleotide includes an oligonucleotide of the sequence of SEQ ID NO: 28:
CC$X_1$$X_2$$X_3$$X_4$G$X_5$$X_6$$X_7$G$X_8$G$X_9$$X_{10}$$X_{11}$TA$X_{12}$CA GG$X_{13}$$X_{14}$$X_{15}$$X_{16}$$X_{17}$CTA (SEQ ID NO: 28), $X_1$ is A or G or C or T, $X_2$ is A or G, $X_3$ is G or C or T, $X_4$ is A or G, $X_5$ is A or G or C, $X_6$ is T or A, $X_7$ is A or G, $X_8$ is T or G, $X_9$ is G or A or C, $X_{10}$ is C or T, $X_{11}$ is A or T, $X_{12}$ is G or C or C, $X_{13}$ is G or A, $X_{14}$ is A or G or T or C, $X_{15}$ is T or C or G, $X_{16}$ is T or C and $X_{17}$ is A or C.

In an embodiment, a first primer oligonucleotide includes an oligonucleotide of the sequence of SEQ ID NO: 29:
C$X_1$$X_2$$X_3$$X_4$$X_5$G$X_6$$X_7$$X_8$$X_9$$X_{10}$$X_{11}$ACA$X_{12}$$X_{13}$C$X_{14}$ $X_{15}$ACTAT$X_{16}$$X_{17}$$X_{18}$$X_{19}$T$X_{20}$ (SEQ ID NO: 29), $X_1$ is A or T, $X_2$ is G or A, $X_3$ is C or A or G, $X_4$ is T or C or A, $X_5$ is A or T or G, $X_6$ is G or A, $X_7$ is A or G, $X_8$ is C or T, $X_9$ is T or G or A, $X_{10}$ is A or G, $X_{11}$ is T or A, $X_{12}$ is T or C, $X_{13}$ is T or C, $X_{14}$ is T or C, $X_{15}$ is T or C, $X_{16}$ is T or C, $X_{17}$ is T or A, $X_{18}$ is T or G, $X_{19}$ is A or G and $X_{20}$ is T or C.

In an embodiment, a first primer oligonucleotide includes an oligonucleotide of the sequence of SEQ ID NO: 30:
T$X_1$T$X_2$TG$X_3$T$X_4$TC$X_5$C$X_7$G$X_8$AA$X_9$A$X_{10}$$X_{11}$ CC$X_{12}$G$X_{13}$AAAT$X_{14}$$X_{15}$ (SEQ ID NO: 30), $X_1$ is C or T, $X_2$ is T or C, $X_3$ is C or T, $X_4$ is A or G, $X_5$ is T or C, $X_6$ is T or C, $X_7$ is A or T, $X_8$ is A or T, $X_9$ is G or A, $X_{10}$ is A or G, $X_{11}$ is T or C, $X_{12}$ is A or G, $X_{13}$ is A or T or G, $X_{14}$ is T or G, and $X_{15}$ is T or C or G.

In an embodiment, a first primer oligonucleotide includes an oligonucleotide of the sequence of SEQ ID NO: 31:
$X_1$$X_2$CCTT$X_3$CCA$X_4$$X_5$$X_6$$X_7$GG$X_8$T$X_9$T$X_{10}$TG$X_{11}$ T$X_{12}$TC$X_{13}$CTG$X_{14}$AA$X_{15}$A$X_{16}$$X_{17}$ (SEQ ID NO: 31), $X_1$ is G or A, $X_2$ is T or C, $X_3$ is C or T, $X_4$ is A or G, $X_5$ is A or G, $X_6$ is T or C or G, $X_7$ is A or T or C or G, $X_8$ is A or G, $X_9$ is C or T, $X_{10}$ is C or T, $X_{11}$ is C or T, $X_{12}$ is C or A, $X_{13}$ is C or T, $X_{14}$ is T or A, $X_{15}$ is T or A, $X_{16}$ is A or G and $X_{17}$ is A or G.

The probe may be coupled to a detectable label such as those described above, at one or both of its 3'-end and 5'-end.

In an embodiment, a kit containing a first primer and a second primer, as described above, is provided. The kit further includes a probe as described above. Such kit is suitable and useful for an accurate, sensitive and fast detection of HCV in a sample.

The kit may further contain a reverse transcriptase activity, polymerase activity, and a cleaving agent which is capable of cleaving an internal site of the probe oligonucleotides. The cleaving agent may be selected from the group consisting of an RNase H, a Kamchatka crab duplex specific nuclease, an endonuclease, and a nicking endonuclease. The kit may further contain uracil-N-glycosylase.

According to an embodiment, the method may further include a mixture including dATP, dCTP, dGTP, dTTP, and dUTP; a DNA polymerase; RNase H II; a uracil-N-glycosylase, and a buffer solution.

DETAILED DESCRIPTION OF THE INVENTION

Figure 1:
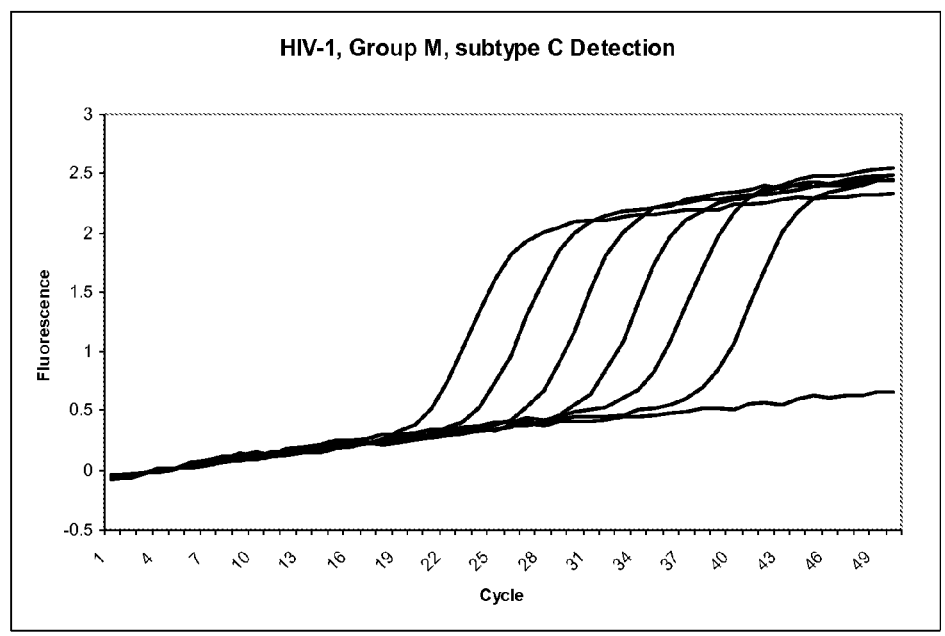
FIG. 1 depicts RT-PCR amplification of 10 fold serial dilutions of HIV-1, Group M, subtype C RNA according to the preferred embodiment of the invention.

The practice of the embodiments described herein employs, unless otherwise indicated, conventional molecular biological techniques within the skill of the art. Such techniques are well known to the skilled worker, and are explained fully in the literature. See, e.g., Ausubel, et al., ed., Current Protocols in Molecular Biology, John Wiley & Sons, Inc., NY, N.Y. (1987-2008), including all supplements; Sambrook, et al., Molecular Cloning: A Laboratory Manual, 2nd Edition, Cold Spring Harbor, N.Y. (1989).

Unless defined otherwise, all technical and scientific terms used herein have the same meaning as is commonly understood by one of skill in the art. The specification also provides definitions of terms to help interpret the disclosure and claims of this application. In the event a definition is not consistent with definitions elsewhere, the definition set forth in this application will control.

A "target DNA or "target RNA"" or "target nucleic acid," or "target nucleic acid sequence" refers to a nucleic acid that is targeted for DNA amplification. A target nucleic acid sequence serves as a template for amplification in a PCR reaction or reverse transcriptase-PCR reaction. Target nucleic acid sequences may include both naturally occurring and synthetic molecules. Exemplary target nucleic acid sequences include, but are not limited to, genomic DNA or genomic RNA.

The "polynucleotide" used herein is a double-stranded DNA or cDNA, or a single-stranded DNA or RNA and includes nucleotide analogues unless otherwise stated.

The "probe" used herein is a modified linear oligomer which includes a deoxyribonucleotide and/or a ribonucleotide backbone which may be hybridized with a specific polynucleotide sequence. Furthermore, the probe is labeled with a detectable marker whose signal is modified in the presence of amplicon either through direct hybridization or by hybridization combined with enzyme mediated processing. The probe may be single or double stranded.

A probe according to an embodiment may include a sequence that is perfectly complementary to a polynucleotide template or a substantially complementary sequence that does not inhibit specific hybridization. Conditions suitable for the hybridization are described above.

As used herein, the term "substantially complementary" refers to two nucleic acid strands that are sufficiently complimentary in sequence to anneal and form a stable duplex. The complementarity does not need to be perfect; there may be any number of base pair mismatches, for example, between the two nucleic acids. However, if the number of mismatches is so great that no hybridization can occur under even the least stringent hybridization conditions, the sequence is not a substantially complementary sequence. When two sequences are referred to as "substantially complementary" herein, it means that the sequences are sufficiently complementary to each other to hybridize under the selected reaction conditions. The relationship of nucleic acid complementarity and stringency of hybridization sufficient to achieve specificity is well known in the art. Two substantially complementary strands can be, for example, perfectly complementary or can contain from 1 to many mismatches so long as the hybridization conditions are sufficient to allow, for example discrimination between a pairing sequence and a non-pairing sequence. Accordingly, "substantially complementary" sequences can refer to sequences with base-pair complementarity of 100, 95, 90, 80, 75, 70, 60, 50 percent or less, or any number in between, in a double-stranded region.

The "substantially complementary sequence" used herein may also mean a sequence that may be hybridized with the template polynucleotide under stringent conditions that are known in the art. The "stringent conditions" used herein are disclosed in Joseph Sambrook, et al., *Molecular Cloning, A Laboratory Manual*, Cold Spring Harbor Laboratory Press, Cold Spring Harbor, N.Y. (2001) and Haymes, B. D., et al., *Nucleic Acid Hybridization, A Practical Approach*, IRL Press, Washington, D.C. (1985), and may be determined by controlling temperature, ionic strength (concentration of a buffer solution), and the existence of a compound such as an organic solvent.

The "primer" used herein is a single-stranded oligonucleotide functioning as an origin of polymerization of template DNA under appropriate conditions (i.e., nucleoside triphosphates and DNA polymerase(s)) at a suitable temperature and in a suitable reaction buffer.

The length of the primer may vary according to various factors, for example, temperature and the use of the primer, but the primer is generally 15 to 35 nucleotides in length and hybridizes to a region complementary to its sequence. Generally, a short primer may form a sufficiently stable hybrid complex with its template at a low temperature. As used herein, the term "oligonucleotide" is used sometimes interchangeably with "primer" or "polynucleotide." The "forward primer" and "reverse primer" are primers respectively binding to a 3' end and a 5' end of a specific region of a template that is amplified by PCR.

The sequence of the primer is not required to be completely complementary to a part of the sequence of the template. The primer may have sufficient complimentarity to be hybridized with the template and perform intrinsic functions of the primer. Thus, a primer set according to an embodiment is not required to be completely complementary to the nucleotide sequence of the template. The primer may be designed based on the nucleotide sequence of the template, for example, using a computer program such as Primer Express (Applied Biosystems, Inc.).

A primer according to an embodiment of the invention may be hybridized or annealed to a part of a template to form a double-strand. Conditions for hybridizing nucleic acid suitable for forming the double-stranded structure are disclosed by Joseph Sambrook, et al., Molecular Cloning, A Laboratory Manual, Cold Spring Harbor Laboratory Press, Cold Spring Harbor, N.Y. (2001) and Haymes, B. D., et al., Nucleic Acid Hybridization, A Practical Approach, IRL Press, Washington, D.C. (1985).

According to an embodiment, primers useful for the specific detection of HIV-1 are 10-35 base pairs in length and designed such that amplification products have a size of 50 to 300 base pairs and are suitable for real-time PCR.

In the primer sets and probes for detecting HIV-1 according to an embodiment, the probe may be labeled with different detectable markers. The detectable marker indicates a compound, a biological molecule, biological molecule analogues, or the like which are linked, bound, or attached to the probe so as to identify density, concentration, quantity, or the like using various methods known in the art. For example, the detectable marker may be a fluorescence marker, a luminescent material, a bioluminescent material, an isotope, or the like, but is not limited thereto.

According to an embodiment, the 5' end of the probe may be labeled with a fluorescence marker (e.g., commercially available fluorescent markers distributed under names FAM, VIC, TET, JOE, HEX, CY3, CY5, ROX, RED610, TEXAS RED, RED670, and NED), and the 3' end of the probe may be labeled with a fluorescence quencher (e.g., commercially available fluorescent markers distributed under tradenames: 6 TAMRA, BHQ-1,2,3), and a molecular groove binding non-fluorescence quencher such as MGBNFQ™. Excitation and emission wavelengths vary according to the type of the fluorescence marker, and the use of the fluorescence marker also varies. The probe may be labeled with the fluorescence marker using various methods that are known in the art. A CATACLEAVE™ probe according to an embodiment may have the 5' end labeled with a fluorescence marker, e.g., FAM® and the 3' end labeled with a fluorescence quencher, e.g., TAMRA®, and may be added to a PCR reaction solution. Fluorescence emission of the CATACLEAVE™ probe is described above.

According to a preferred embodiment the probe may undergo enonucleolytic enzymatic processing that such that emission from the detectable marker is enhanced in the presence of amplicon. One example of such a probe is a CATACLEAVE™ probe. The CATACLEAVE™ probe is disclosed in detail in *Anal. Biochem.* 333:246-255, 2004 and U.S. Pat. No. 6,787,304, the contents of which are entirely incorporated herein by reference.

According to an embodiment the CATACLEAVE™ probe is a single stranded polynucleotide that has an enzyme mediated cleavable site which is the target of an endonuclease, such as a restriction enzyme or RNase H.

According to an embodiment, the probe has a chimeric structure where the 5' and 3' ends of the probe are constructed of DNA and the cleavage site contains RNA. The DNA sequence portions of the probe are labeled with a (FRET) pair either at the ends or internally. Emission from the donor is quenched by FRET in the unprocessed state. In a real-time PCR assay including the probe, the reaction includes an RNase H enzyme that will specifically cleave the RNA sequence portion of the probe when hybridized to a DNA template. Hybridization generally occurs at temperatures similar to that used in the TaqMan reaction. When the RNA sequence portion of the probe is cleaved by the enzyme, the two parts of the probe, i.e., a donor and an acceptor, dissociate from the target amplicon at the reaction temperature and diffuse into the reaction buffer. The increased distance of separation between the donor and acceptor causes a reversal of FRET and an increase in donor emission that is proportional to the number of amplicons and can be monitored in real time. Cleavage and dissociation regenerates a site for further CATACLEAVE™ probe binding on the amplicon. In this way, it is possible for a single amplicon to serve as a target for multiple rounds of probe cleavage until the primer is extended through the CATACLEAVE™ probe binding site.

According to an embodiment, there is provided a method for detecting group M, O, and N HIV-1 in a sample. Representative clinical isolates are selected from the group consisting of HIV-11-2496, HIV-1 BK132, HIV-1 DJ259, HIV-1 SE365, HIV-1 UG274, HIV-1 42368, HIV-1 BZ126, HIV-1 BZ162, HIV-1 POC44951, HIV-1 HH8793, HIV-1 BCF-KITA, HIV-1 I-2481, HIV-1 BCF06, and HIV-1 BCF11, but are not limited thereto.

Oligonucleotides may be synthesized and prepared by any suitable methods (such as chemical synthesis), which are known in the art. Oligonucleotides may also be conveniently available through commercial sources.

The terms "annealing" and "hybridization" are used interchangeably and mean the base-pairing interaction of one nucleic acid with another nucleic acid that results in formation of a duplex, triplex, or other higher-ordered structure. In certain embodiments, the primary interaction is base specific, e.g., A/T and G/C, by Watson/Crick and Hoogsteen-type hydrogen bonding. In certain embodiments, base-stacking and hydrophobic interactions may also contribute to duplex stability.

A person of skill in the art will know how to design PCR primers flanking a HIV-1 genomic sequence of interest. Synthesized oligos are typically between 20 and 26 base pairs in length with a melting temperature, $T_M$ of around 55 degrees.

As used herein, "label" or "detectable label" can refer to any chemical moiety attached to a nucleotide, nucleotide polymer, or nucleic acid binding factor, wherein the attachment may be covalent or non-covalent. Preferably, the label is detectable and renders said nucleotide or nucleotide polymer detectable to the practitioner of the invention. Detectable labels include luminescent molecules, chemiluminescent molecules, fluorochromes, fluorescent quenching agents, colored molecules, radioisotopes or scintillants. Detectable labels also include any useful linker molecule (such as biotin, avidin, streptavidin, HRP, protein A, protein G, antibodies or fragments thereof, Grb2, polyhistidine, $Ni^{2+}$, FLAG tags, myc tags), heavy metals, enzymes (examples include alkaline phosphatase, peroxidase and luciferase), electron donors/acceptors, acridinium esters, dyes and calorimetric substrates. It is also envisioned that a change in mass may be considered a detectable label, as is the case of surface plasmon resonance detection. The skilled artisan would readily recognize useful detectable labels that are not mentioned above, which may be employed in the operation of the present invention.

The uracil-N-glycosylase may be one obtained from psychrophilic marine bacterium BMTU 3346, *Psychrobacter* species HJ147, or an *Bacillus* species HJ141, or a mutant thereof as long as the mutant maintains the activity of uracil-N-glycosylase.

The DNA polymerase may be obtained from a source such as *Thermus aquaticis*, an *Thermococcus litoralis*, an *Pyrococcus furiosis*, an *Thermus flavus*, an *Thermus thermophilis*, an *Pyrococcus woesei*, an *Thermus ubiquitous*, an *Thermus litoralis*, an *Thermotoga maritime*, or an *Thermus filiformis*, or a mutant thereof as long as the mutant maintains the activity of DNA polymerase.

The reverse transcriptase may be one obtained from an Avian Myeloblastosis Virus or an Moloney Murine Leukemia Virus, or a mutant thereof as long as the mutant maintains the activity of DNA polymerase.

The cleaving agent may be selected from the group consisting of an RNase H, an Kamchatka crab duplex specific nuclease, an endonuclease, an nicking endonuclease, an exonuclease, or an enzyme containing nuclease activity.

The deoxynucleoside triphosphate mixture contains deoxyuridine triphosphate in addition to, or substituted for, deoxythymidine triphosphate.

The enzyme mediated cleavable sequence is at least one of a ribonucleic acid (RNA) and a deoxyribonucleic (DNA) acid.

The cleaving site may be located in a position which allows for the activation of the detectable marker upon cleavage of the probe.

The plurality of nucleic acid probes may further include a first probe region and a second probe region connected with the enzyme mediated cleavable sequence.

The first probe region may be at least one of a ribonucleic acid (RNA) and a deoxyribonucleic acid (DNA) and the second probe region is at least one of a ribonucleic acid (RNA) and a deoxyribonucleic acid (DNA).

The detectable marker may be at least one of attached at the 5' end of the first probe region, 3' end of the first probe region, 5' end of the second probe region, 3' end of the second probe region, internally within either the first probe region or second probe region, 5' end of the enzyme mediated cleavable sequence, 3' end of the enzyme mediated cleavable sequence, and internally within the enzyme mediate cleavable sequence.

The detectable marker may be selected from the group consisting of a fluorescent molecule, radioisotopes, enzymes, or chemilumenescent catalysts.

The detectable marker may be at least one of an internally labeled Forster resonance energy transfer (FRET) pair, externally labeled FRET pair, and a FRET pair attached at a 3' end of the first probe region and a 5' end of the second probe region.

In an embodiment, a kit containing a forward primer and a reverse primer, as described above, is provided. The kit further includes a probe as described above. Such kit is suitable and useful for an accurate, sensitive and fast detection of a target HIV-1 gene in a sample.

The kit may further contain a reverse transcriptase activity, polymerase activity, and a cleaving agent which is capable of cleaving an internal site of the probe oligonucleotides. The cleaving agent may be selected from the group consisting of an RNase H, an Kamchatka crab duplex specific nuclease, an endonuclease, and an nicking endonuclease. The kit may further contain uraci-N-glycosylase, as explained above.

According to an embodiment, the probe may be a hybridization probe such as a molecular beacon.

According to an embodiment the molecular beacon is a single stranded polynucleotide labeled with donor and acceptor labels forming a fluorescence resonance energy transfer (FRET) pair. One such example of a FRET pair is FAM® and TAMRA®. In the unhybridized state the molecular beacon forms a secondary structure such that the donor and quencher moieties are positioned to permit efficient FRET and the donor emission signal is low. The probe is designed so that in the presence of amplicon the probe will unfold and hybridize to the target. The increased distance of separation between the donor and quencher causes a reversal of FRET and an increase in donor emission that is proportional to the number of amplicons and can be monitored in real time.

According to a further embodiment, the probe may undergo exonucleolytic enzymatic processing such that emission from the detectable marker is enhanced in the presence of amplicon. One example of such a probe is a TAQMAN® probe.

According to an embodiment the TAQMAN® probe is a linear polynucleotide labeled with a fluorescence donor at the 5' end and a quencher molecule at the 3' end. Emission from the donor is quenched by FRET in the unprocessed state. In a regular PCR reaction cycle, the temperature is first increased to cause denaturation of the template and amplicons. The temperature is then decreased to permit specific hybridization of the primers and TAQMAN® probe to the template. DNA polymerase extends both primers to synthesize additional amplicon. During extension the polymerase encounters the 5' end of the TAQMAN® probe and the 5'→3' exonuclease activity of the polymerase begins to degrade the probe from the 5' end into mononucleotides. This enzymatic processing activity releases the fluorescence donor into the reaction medium. The increased distance of separation between the donor and acceptor causes a reversal of FRET and an increase in donor emission that is proportional to the number of amplicons and can be monitored in real time.

According to another embodiment, there is provided a method of detecting HIV-1, the method including: isolating total RNA from a sample; performing a real-time PCR by mixing the isolated total RNA and associated reaction components; and identifying the existence of HIV-1 based on the results of the real-time PCR.

The previously described embodiments have many advantages, including the ability to detect HIV-1 nucleic acid sequences in a sample in real-time. The detection method is fast, accurate and suitable for high throughput applications.

Amplification

Once the RNA is isolated from a sample and the primers are selected, nucleic acid amplification can be accomplished by a variety of methods, including the polymerase chain reaction (PCR), nucleic acid sequence based amplification (NASBA), ligase chain reaction (LCR), and rolling circle amplification (RCA)(U.S. Pat. No. 5,871,921), Cleavage Fragment Length Polymorphism (U.S. Pat. No. 5,719,028), Isothermal and Chimeric Primer-initiated Amplification of Nucleic Acid (ICAN), Ramification-extension Amplification Method (U.S. Pat. Nos. 5,719,028 and 5,942,391) or other suitable methods for amplification of DNA. The polymerase chain reaction (PCR) is the method most commonly used to amplify specific target DNA sequences.

"Polymerase chain reaction," or "PCR," generally refers to a method for amplification of a desired nucleotide sequence in vitro. The procedure is described in detail in U.S. Pat. Nos. 4,683,202, 4,683,195, 4,800,159, and 4,965,188, the contents of which are hereby incorporated herein in their entirety. Generally, the PCR process consists of introducing a molar excess of two or more extendable oligonucleotide primers to a reaction mixture comprising the desired target sequence(s), where the primers are complementary to opposite strands of the double stranded target sequence. The reaction mixture is subjected to a program of thermal cycling in the presence of a DNA polymerase, resulting in the amplification of the desired target sequence flanked by the DNA primers.

The DNA polymerase may be a thermally stable DNA polymerase obtained from *Thermus aquaticus* (Taq), *Thermus thermophilus* (Tth), *Thermus filifbrmis*, *Thermis flavus*, *Thermococcus litoralis*, *Pyrococcus woesei*, *Thermus ubiquitous*, *Thermus litoralis*, *Thermotoga maritime*, *Thermus filifbrmis*, or *Pyrococcus furiosus* (Pfu). In addition, RNase H includes a thermally stable RNase H enzyme such as *Pyrococcus furiosus* RNase H II, *Pyrococcus horikoshi* RNase H II, *Thermococcus litoralis* RNase HIII, or *Thermus thermophilus* RNase HI, but is not limited thereto. The buffer solution is added to change stability, activity and/or lifetime of at least one component involved in the amplification reaction. The buffer solution is well known in the art and may be Tris, Tricine, MOPS, or HEPES, but is not limited thereto. The primer set and probe may be packed in a single reaction container, strip, or microplate by using various methods known in the art.

One of the most widely used techniques to study gene expression exploits first-strand cDNA for mRNA sequence(s) as template for amplification by the PCR. This method, often referred to as reverse transcriptase—PCR, exploits the high sensitivity and specificity of the PCR process and is widely used for detection and quantification of RNA.

The reverse transcriptase-PCR procedure, carried out as either an end-point or real-time assay, involves two separate molecular syntheses: (i) the synthesis of cDNA from an RNA template; and (ii) the replication of the newly synthesized cDNA through PCR amplification. To attempt to address the technical problems often associated with reverse transcriptase-PCR, a number of protocols have been developed taking into account the three basic steps of the procedure: (a) the denaturation of RNA and the hybridization of reverse primer; (b) the synthesis of cDNA; and (c) PCR amplification. In the so called "uncoupled" reverse transcriptase-PCR procedure (e.g., two step reverse transcriptase-PCR), reverse transcription is performed as an independent step using the optimal buffer condition for reverse transcriptase activity. Following cDNA synthesis, the reaction is diluted to decrease $MgCl_2$, and deoxyribonucleoside triphosphate (dNTP) concentrations to conditions optimal for Taq DNA Polymerase activity, and PCR is carried out according to standard conditions (see U.S. Pat. Nos. 4,683,195 and 4,683,202). By contrast, "coupled" reverse transcriptase PCR methods use a common buffer for reverse transcriptase and Taq DNA Polymerase activities. In one version, the annealing of reverse primer is a separate step preceding the addition of enzymes, which are then added to the single reaction vessel. In another version, the reverse transcriptase activity is a component of the thermostable Tth DNA polymerase. Annealing and cDNA synthesis are performed in the presence of $Mn^{2+}$ then PCR is carried out in the presence of $Mg^{2+}$ after the removal of $Mn^{2+}$ by a chelating agent. Finally, the "continuous" method (e.g., one step reverse transcriptase-PCR) integrates the three reverse transcriptase-PCR steps into a single continuous reaction that avoids the opening of the reaction tube for component or enzyme addition. Continuous reverse transcriptase-PCR has been described as a single enzyme system using the reverse transcriptase activity of thermostable Taq DNA Polymerase and Tth polymerase and as a two enzyme system using AMV reverse transcriptase and Taq DNA Polymerase wherein the initial 65° C. RNA denaturation step was omitted.

The first step in real-time, reverse-transcription PCR is to generate the complementary DNA strand using one of the template specific DNA primers. In traditional PCR reactions this product is denatured, the second template specific primer binds to the cDNA, and is extended to form duplex DNA. This product is amplified in subsequent rounds of temperature cycling. To maintain the highest sensitivity it is important that the RNA not be degraded prior to synthesis of cDNA. The presence of RNase H in the reaction buffer will cause unwanted degradation of the RNA:DNA hybrid formed in the first step of the process because it can serve as a substrate for the enzyme. There are two major methods to combat this issue. One is to physically separate the RNase H from the rest of the reverse-transcription reaction using a barrier such as wax that will melt during the initial high temperature DNA denaturation step. A second method is to modify the RNase H such that it is inactive at the reverse-transcription temperature, typically 45-55° C. Several methods are known in the art, including reaction of RNase H with an antibody, or reversible chemical modification. Various RNase H enzymes that can be used in the invention are explained are described in more detail hereinafter.

Additional examples of RNase H enzymes that can be employed in the invention are described in U.S. Patent Application No. 2009/0325169 to Walder et al.

One step reverse transcriptase-PCR provides several advantages over uncoupled reverse transcriptase-PCR. One step reverse transcriptase-PCR requires less handling of the reaction mixture reagents and nucleic acid products than uncoupled reverse transcriptase-PCR (e.g., opening of the reaction tube for component or enzyme addition in between the two reaction steps), and is therefore less labor intensive, reducing the required number of person hours. One step reverse transcriptase-PCR also requires less sample, and reduces the risk of contamination. The sensitivity and specificity of one-step reverse transcriptase-PCR has proven well suited for studying expression levels of one to several genes in a given sample or the detection of pathogen RNA. Typically, this procedure has been limited to use of gene-specific primers to initiate cDNA synthesis.

The ability to measure the kinetics of a PCR reaction by real-time detection in combination with these reverse transcriptase-PCR techniques has enabled accurate and precise determination of RNA copy number with high sensitivity. This has become possible by detecting the reverse transcriptase-PCR product through fluorescence monitoring and measurement of PCR product during the amplification process by fluorescent dual-labeled hybridization probe technologies, such as the 5' fluorogenic nuclease assay ("TAQMAN®") or endonuclease assay ("CATACLEAVE™").

Real-time methods have been developed to monitor amplification during the PCR process. These methods typically employ fluorescently labeled probes that bind to the newly synthesized DNA or dyes whose fluorescence emission is increased when intercalated into double stranded DNA.

Real-Time PCR of an HIV-1 Target Nucleic Acid Sequence Using a CATACLEAVE™ Probe In one embodiment, the probes are designed so that donor emission is quenched in the absence of target by fluorescence resonance energy transfer (FRET) between two chromophores. The donor chromophore, in its excited state, may transfer energy to an acceptor chromophore when the pair is in close proximity. This transfer is always non-radiative and occurs through dipole-dipole coupling. Any process that sufficiently increases the distance between the chromophores will decrease FRET efficiency such that the donor chromophore emission can be detected radiatively. Common donor chromophores include FAM®, TAMRA®, VIC®, JOE®, CY3®, CY5®, and TEXAS RED®. Acceptor chromophores are chosen so that their excitation spectra overlap with the emission spectrum of the donor. An example of such a pair is FAM®-TAMRA®. There are also non fluorescent acceptors that will quench a wide range of donors. Other examples of appropriate donor-acceptor FRET pairs will be known to those skilled in the art.

Common examples of FRET probes that can be used for real-time detection of PCR include molecular beacons, TAQMAN® probes (e.g., U.S. Pat. Nos. 5,210,015 and 5,487,972), and CATACLEAVE™ probes (e.g., U.S. Pat. No. 5,763,181). The molecular beacon is a single stranded oligonucleotide designed so that in the unbound state the probe forms a secondary structure where the donor and acceptor chromophores are in close proximity and donor emission is reduced. At the proper reaction temperature the beacon unfolds and specifically binds to the amplicon. Once unfolded the distance between the donor and acceptor chromophores increases such that FRET is reversed and donor emission can be monitored using specialized instrumentation. TAQMAN® and CATACLEAVE™ technologies differ from the molecular beacon in that the FRET probes employed are cleaved such that the donor and acceptor chromophores become sufficiently separated to reverse FRET.

TAQMAN® technology employs a single stranded oligonucleotide probe that is labeled at the 5' end with a donor chromophore and at the 3' end with an acceptor chromophore. The DNA polymerase used for amplification must contain a 5'→3' exonuclease activity. The TAQMAN® probe binds to one strand of the amplicon at the same time that the primer binds. As the DNA polymerase extends the primer the polymerase will eventually encounter the bound TAQMAN® probe. At this time the exonuclease activity of the polymerase will sequentially degrade the TAQMAN® probe starting at the 5' end. As the probe is digested the mononucleotides comprising the probe are released into the reaction buffer. The donor diffuses away from the acceptor and FRET is reversed. Emission from the donor is monitored to identify probe cleavage. Because of the way TAQMAN® works a specific amplicon can be detected only once for every cycle of PCR. Extension of the primer through the TAQMAN® target site generates a double stranded product that prevents further binding of TAQMAN® probes until the amplicon is denatured in the next PCR cycle.

U.S. Pat. No. 5,763,181, the content of which is incorporated herein by reference, describes another real-time detection method (referred to as "CATACLEAVE™"). CATACLEAVE™ technology differs from TAQMAN® in that cleavage of the probe is accomplished by a second enzyme that does not have polymerase activity. The CATACLEAVE™ probe has a sequence within the molecule which is a target of an endonuclease, such as, for example a restriction enzyme or RNAase. In one example, the CATACLEAVE™ probe has a chimeric structure where the 5' and 3' ends of the probe are constructed of DNA and the cleavage site contains RNA. The DNA sequence portions of the probe are labeled with a FRET pair either at the ends or internally. The PCR reaction includes an RNase H enzyme that will specifically cleave the RNA sequence portion of a RNA-DNA duplex. After cleavage, the two halves of the probe dissociate from the target amplicon at the reaction temperature and diffuse into the reaction buffer. As the donor and acceptors separate FRET is reversed in the same way as the TAQMAN® probe and donor emission can be monitored. Cleavage and dissociation regenerates a site for further CATACLEAVE™ binding. In this way it is possible for a single amplicon to serve as a target for multiple rounds of probe cleavage until the primer is extended through the CATACLEAVE™ probe binding site.

Labeling of a HIV 1-Specific CATACLEAVE™ Probe

The term "probe" comprises a polynucleotide that comprises a specific portion designed to hybridize in a sequence-specific manner with a complementary region of a specific nucleic acid sequence, e.g., a target nucleic acid sequence. In one embodiment, the oligonucleotide probe is in the range of 15-60 nucleotides in length. More preferably, the oligonucleotide probe is in the range of 18-45 nucleotides in length. The precise sequence and length of an oligonucleotide probe of the invention depends in part on the nature of the target polynucleotide to which it binds. The binding location and length may be varied to achieve appropriate annealing and melting properties for a particular embodiment. Guidance for making such design choices can be found in many of the references describing TAQMAN® assays or CATACLEAVE™, described in U.S. Pat. Nos. 5,763,181, 6,787,304, and 7,112,422, the contents of which contents are incorporated herein by reference in their entirety.

As used herein, a "label" or "detectable label" may refer to any label of a CATACLEAVE™ probe comprising a fluorochrome compound that is attached to the probe by covalent or non-covalent means.

As used herein, "fluorochrome" refers to a fluorescent compound that emits light upon excitation by light of a shorter wavelength than the light that is emitted. The term "fluorescent donor" or "fluorescence donor" refers to a fluorochrome that emits light that is measured in the assays described in the present invention. More specifically, a fluorescent donor provides energy that is absorbed by a fluorescence acceptor. The term "fluorescent acceptor" or "fluorescence acceptor" refers to either a second fluorochrome or a quenching molecule that absorbs energy emitted from the fluorescence donor. The second fluorochrome absorbs the energy that is emitted from the fluorescence donor and emits light of longer wavelength than the light emitted by the fluorescence donor. The quenching molecule absorbs energy emitted by the fluorescence donor.

Any luminescent molecule, preferably a fluorochrome and/or fluorescent quencher may be used in the practice of this invention. For example, commercially available fluorochromes and/or fluorescent quenchers distributed under tradenames: ALEXA FLUOR™ 350, ALEXA FLUOR™ 430, ALEXA FLUOR™ 488, ALEXA FLUOR™ 532, ALEXA FLUOR™ 546, ALEXA FLUOR™ 568, ALEXA FLUOR™ 594, ALEXA FLUOR™ 633, ALEXA FLUOR™ 647, ALEXA FLUOR™ 660, ALEXA FLUOR™ 680, 7-diethylaminocoumarin-3-carboxylic acid, Fluorescein, OREGON GREEN™ 488, OREGON GREEN™ 514, Tetramethylrhodamine, Rhodamine X, TEXAS RED™ dye, QSY 7™, QSY33™, Dabcyl, BODIPY FL™, BODIPY 630/650™, BODIPY 6501665™, BODIPY TMR-X™, BODIPY TR-X™, Dialkylaminocoumarin, CY5.5™, CY5™, CY3.5™, CY3™, DTPA($Eu^{3+}$)-AMCA and TTHA($Eu^{3+}$) AMCA may be used.

In one embodiment, the 3' terminal nucleotide of the oligonucleotide probe is blocked or rendered incapable of extension by a nucleic acid polymerase. Such blocking is conveniently carried out by the attachment of a reporter or quencher molecule to the terminal 3' position of the probe.

In one embodiment, reporter molecules are fluorescent organic dyes derivatized for attachment to the terminal 3' or terminal 5' ends of the probe via a linking moiety. Preferably, quencher molecules are also organic dyes, which may or may not be fluorescent, depending on the embodiment of the invention. For example, in a preferred embodiment of the invention, the quencher molecule is non-fluorescent. Generally whether the quencher molecule is fluorescent or simply releases the transferred energy from the reporter by non-radiative decay, the absorption band of the quencher should substantially overlap the fluorescent emission band of the reporter molecule. Non-fluorescent quencher molecules that absorb energy from excited reporter molecules, but which do not release the energy radiatively, are referred to in the application as chromogenic molecules.

Exemplary reporter-quencher pairs may be selected from xanthene dyes, including fluoresceins, and rhodamine dyes. Many suitable forms of these compounds are widely available commercially with substituents on their phenyl moieties which can be used as the site for bonding or as the bonding functionality for attachment to an oligonucleotide. Another group of fluorescent compounds are the naphthylamines, having an amino group in the alpha or beta position. Included among such naphthylamino compounds are 1-dimethylaminonaphthyl-5-sulfonate, 1-anilino-8-naphthalene sulfonate and 2-p-touidinyl6-naphthalene sulfonate. Other dyes include 3-phenyl-7-isocyanatocoumarin, acridines, such as 9-isothiocyanatoacridine and acridine orange; N-(p-(2-benzoxazolyl)phenyl)maleimide; benzoxadiazoles, stilbenes, pyrenes, and the like.

In one embodiment, reporter and quencher molecules are selected from fluorescein and non-fluorescent quencher dyes.

There are many linking moieties and methodologies for attaching reporter or quencher molecules to the 5' or 3' termini of oligonucleotides, as exemplified by the following references: Eckstein, editor, Oligonucleotides and Analogues: A Practical Approach (IRL Press, Oxford, 1991); Zuckerman et al., Nucleic Acids Research, 15: 5305-5321 (1987) (3' thiol group on oligonucleotide); Sharma et al., Nucleic Acids Research, 19: 3019 (1991) (3' sulfhydryl); Giusti et al., PCR Methods and Applications, 2: 223-227 (1993) and Fung et al., U.S. Pat. No. 4,757,141 (5' phosphoamino group via Aminolink. II available from Applied Biosystems, Foster City, Calif.) Stabinsky, U.S. Pat. No. 4,739,044 (3' aminoalkylphosphoryl group); Agrawal et al., Tetrahedron Letters, 31: 1543-1546 (1990) (attachment via phosphoramidate linkages); Sproat et al., Nucleic Acids Research, 15: 4837 (1987) (5' mercapto group); Nelson et al., Nucleic Acids Research, 17: 7187-7194 (1989) (3' amino group); and the like.

Rhodamine and non-fluorescent quencher dyes are also conveniently attached to the 3' end of an oligonucleotide at the beginning of solid phase synthesis, e.g., Woo et al., U.S. Pat. No. 5,231,191; and Hobbs, Jr., U.S. Pat. No. 4,997,928.

Real-Time Detection of HIV-1 Target Nucleic Acid Sequences Using a CATACLEAVE™ Probe The labeled oligonucleotide probe may be used as a probe for the real-time detection of HIV-1 target nucleic acid sequence in a sample.

A CATACLEAVE™ oligonucleotide probe is first synthesized with DNA and RNA sequences that are complimentary to sequences found within a PCR amplicon comprising a selected HIV-1 target sequence. In one embodiment, the probe is labeled with a FRET pair, for example, a fluorescein molecule at one end of the probe and a non-fluorescent quencher molecule at the other end. Hence, upon hybridization of the probe with the PCR amplicon, a RNA:DNA heteroduplex forms that can be cleaved by an RNase H activity.

RNase H hydrolyzes RNA in RNA-DNA hybrids. This enzyme was first identified in calf thymus but has subsequently been described in a variety of organisms. RNase H activity appears to be ubiquitous in eukaryotes and bacteria. Although RNase H's constitute a family of proteins of varying molecular weight and nucleolytic activity, substrate requirements appear to be similar for the various isotypes. For example, most RNase H's studied to date function as endonucleases and requiring divalent cations (e.g., $Mg^{2+}$, $Mn^{2+}$) to produce cleavage products with 5' phosphate and 3' hydroxyl termini.

RNase HI from *E. coli* is the best-characterized member of the RNase H family. In addition to RNase HI, a second *E. coli*

RNase H, RNase HII has been cloned and characterized (Itaya, M., Proc. Natl. Acad. Sci. USA, 1990, 87, 8587-8591). RNase HII is comprised of 213 amino acids while RNase HI is 155 amino acids long. *E. coli* RNase HII displays only 17% homology with *E. coli* RNase HI. An RNase H cloned from *S. typhimurium* differed from *E. coli* RNase HI in only 11 positions and was 155 amino acids in length (Itaya, M. and Kondo K., Nucleic Acids Res., 1991, 19, 4443-4449).

Proteins that display RNase H activity have also been cloned and purified from a number of viruses, other bacteria and yeast (Wintersberger, U. Pharmac. Ther., 1990, 48, 259-280). In many cases, proteins with RNase H activity appear to be fusion proteins in which RNase H is fused to the amino or carboxy end of another enzyme, often a DNA or RNA polymerase. The RNase H domain has been consistently found to be highly homologous to *E. coli* RNase HI, but because the other domains vary substantially, the molecular weights and other characteristics of the fusion proteins vary widely.

In higher eukaryotes two classes of RNase H have been defined based on differences in molecular weight, effects of divalent cations, sensitivity to sulfhydryl agents and immunological cross-reactivity (Busen et al., Eur. J. Biochem., 1977, 74, 203-208). RNase HI enzymes are reported to have molecular weights in the 68-90 kDa range, be activated by either $Mn^{2+}$ or $Mg^{2+}$ and be insensitive to sulfhydryl agents. In contrast, RNase H II enzymes have been reported to have molecular weights ranging from 31-45 kDa, to require $Mg^{2+}$ to be highly sensitive to sulfhydryl agents and to be inhibited by $Mn^{2+}$ (Busen, W., and Hausen, P., Eur. J. Biochem., 1975, 52, 179-190; Kane, C. M., Biochemistry, 1988, 27, 3187-3196; Busen, W., J. Biol. Chem., 1982, 257, 7106-7108.).

An enzyme with RNase HII characteristics has been purified to near homogeneity from human placenta (Frank et al., Nucleic Acids Res., 1994, 22, 5247-5254). This protein has a molecular weight of approximately 33 kDa and is active in a pH range of 6.5-10, with a pH optimum of 8.5-9. The enzyme requires $Mg^{2+}$ and is inhibited by $Mn^{2+}$ and n-ethyl maleimide. The products of cleavage reactions have 3' hydroxyl and 5' phosphate termini.

According to an embodiment, real-time nucleic acid amplification is performed on a target polynucleotide in the presence of a thermo stable nucleic acid polymerase, an RNase H activity, a pair of PCR amplification primers capable of hybridizing to the HIV-1 target polynucleotide, and the labeled CATACLEAVE™ oligonucleotide probe. During the real-time PCR reaction, cleavage of the probe by RNase H leads to the separation of the fluorescent donor from the fluorescent quencher and results in the real-time increase in fluorescence of the probe corresponding to the real-time detection of HIV-1 target DNA sequences in the sample.

Figure 7:
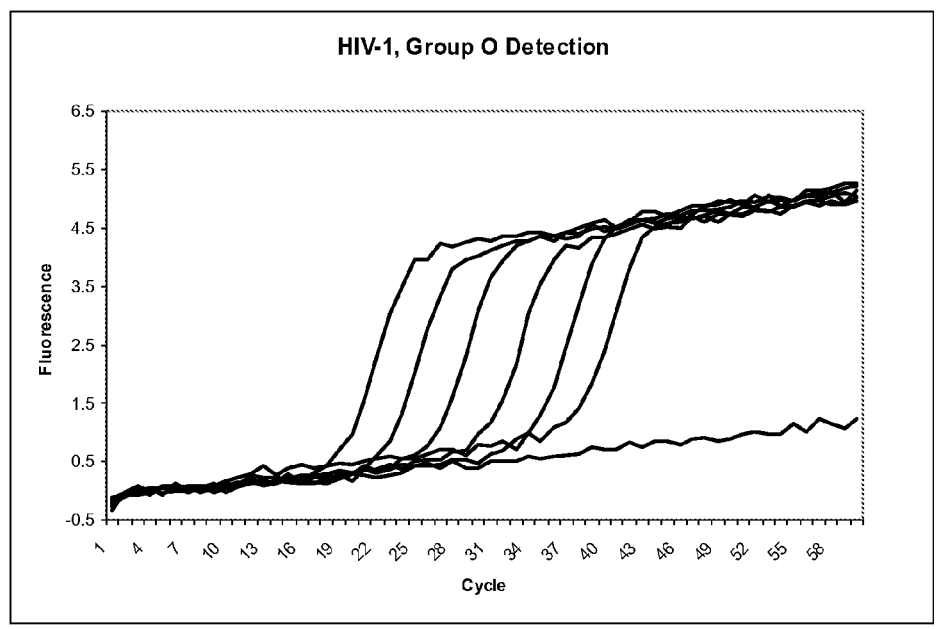
FIG. 7 depicts RT-PCR amplification of 10 fold serial dilutions of HIV-1, Group O RNA according to an embodiment of the invention.

In certain embodiments, the real-time nucleic acid amplification permits the real-time detection of a single target DNA molecule in less than about 40 PCR amplification cycles as shown in FIG. 7.

Exemplary real-time detection of HIV-1 gene sequences in a sample

First, the method includes isolating total RNA from a sample. The method may be applied to a sample that is assumed to be infected with HIV-1. The sample may include cultured cells and animal or human blood, plasma, serum, sperm, or mucus, but is not limited thereto. The isolation of RNA may be accomplished by various methods known in the art. The methods are disclosed in detail in Joseph Sambrook, et al., Molecular Cloning, A Laboratory Manual, Cold Spring Harbor Laboratory Press, Cold Spring Harbor, N.Y. (2001), of which contents are entirely incorporated herein by reference.

Second, the method includes performing a real-time PCR by mixing the isolated total RNA and associated reaction components.

According to an embodiment, the method may further include performing a reverse transcription of the isolated total RNA before performing the real-time PCR. Since the method is used to detect the RNA virus HIV-1, the isolated RNA needs to be converted into cDNA so that it can be used as a template in real-time PCR. The reverse transcription may be conducted using various reverse transcriptases such as those purified from Avian Myeloblastosis Virus (AMV) or Moloney Murine Leukemia Virus (MMLV) or others that are known in the art.

According to an embodiment, instruments for performing temperature cycling and real time detection of the resultant specific amplified products are available commercially. Such instruments are distributed under names 7900, 7500, and 7300 real-time PCR systems (Applied Biosystems Incorporated), Mx3000p (Stratagene), Chromo 4 (BioRad), and Roche LIGHTCYCLER® 480, but are not limited thereto. While performing real time PCR, these devices monitor changes in emission intensity from the detectable marker and convert that information to graphical and/or numerical information that can be analyzed to determine if the target template is present in the test sample.

In the method of detecting HIV-1 according to an embodiment, the real-time PCR may be performed using various methods that are known in the art. For example, an initial denaturation is performed at 95° C. for 10 minutes, and then a denaturation (at 95° C. for 10 seconds), an annealing and RNase II reaction (at 55° C. for 10 seconds), and an elongation (at 72° C. for 30 seconds) are repeated 60 times. Different groups of HIV-1 that can be detected using the method are described above.

Finally, the method includes identifying the existence of HIV-1 based on the results of the real-time PCR.

The existence of HIV-1 may be identified by calculating a $C_t$ value that is the number of amplification cycles when the emission intensity from the detectable marker reaches a predetermined threshold level. If the $C_t$ value is in the range of 15 to 45, it can be concluded that the sample was contaminated with HIV-1. The $C_t$ value may be automatically calculated by a program of the real-time PCR device.

The present invention will be described in further detail with reference to the following examples. These examples are for illustrative purposes only and are not intended to limit the scope of the invention.

The enzyme "Hot Start" RNase HII used in the Examples is a reversibly modified RNase HII. When the modified enzyme is used in a reaction with a Tris based buffer and the temperature is raised to 95° C. the pH of the solution drops and RNase H activity is restored. This method allows for the inclusion of RNase H in the reaction mixture prior to the initiation of reverse transcription. RNase HII and is described in more detail in a co-pending application No. 61/347,984 filed May 25, 2010, the disclosure of which is incorporated herein by reference in its entirety.

Table 1 depicts the sequences of primers and probes.

Table 3 depicts exemplary combinations of the forward and reverse primers and probes.

EXAMPLES

The present invention will now be illustrated by the following examples, which are not to be considered limiting in any way.

Example 1

Method of Detecting HIV-1 Group M

RNA templates used for detection of HIV-1 Group M were purchased from Seracare Life Sciences and are listed in Table 2. Ten fold serial dilutions of RNA template were prepared in 5 mM HEPES (((4-(2-hydroxyethyl)-1-(piperazineethanesulfonic acid)-KOH, pH 7.8) such that the sample of greatest dilution contained between 1 and 10 copies of RNA template. 2 ul of each dilution was used as RNA template in a one-step RT-PCR reaction with 23 μl of PCR mix. The final concentrations of each component in the RT-PCR reaction were as follows, 1×PCR reaction buffer, 400 μM each dATP, dCTP, dGTP, and dUTP, 200 μM dTTP, 80 nM forward primer (SEQ ID NO: 1), 80 nM reverse primer (SEQ ID NO: 12), 60 nM CATACLEAVE™ probe (SEQ ID NO: 22), 5 u "Hot Start" RNase HII, 0.4 u thermolabile UDG (Bacillus ssp.), 2.5 u Platinum TAQ™ Polymerase (Life Technologies) and 2 u SUPERSCRIPT™ III reverse transcriptase (Life Technologies). The one-step RT-PCR reactions were performed on a LIGHTCYCLIER™ 480 real-time PCR machine (Roche) using the following cycling parameters, 50° C. for 15 min for first strand cDNA synthesis, 95° C. for 5 min to heat inactivate the reverse transcriptase and heat activate the RNase HII and DNA polymerase followed by 50 cycles of denaturation at 95° C. for 10 sec, annealing at 55° C. for 10 sec and elongation at 65° C. for 30 sec. Fluorescence readings were taken at each cycle during the 65° C. elongation step.

Figure 2:
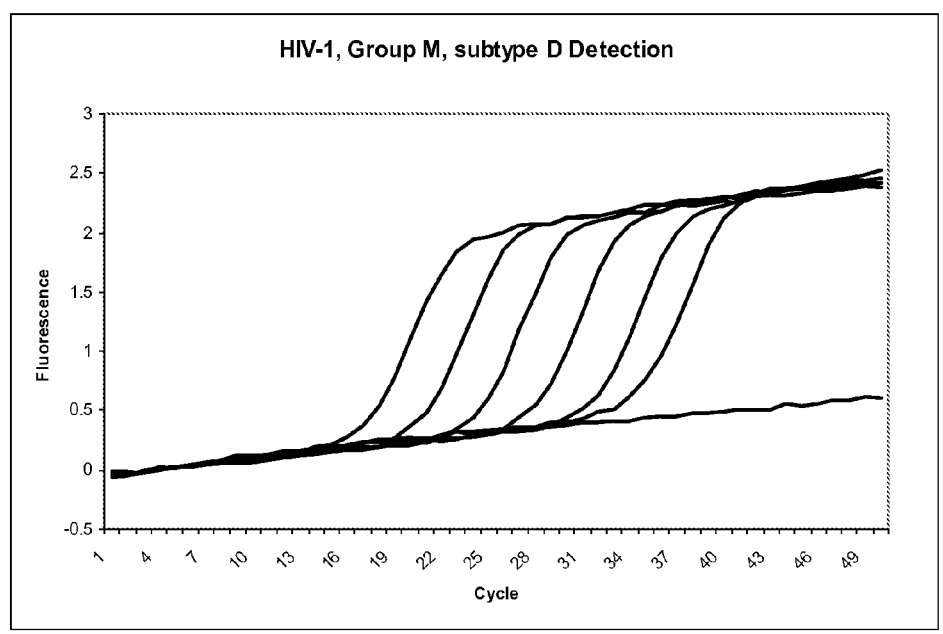
FIG. 2 depicts RT-PCR amplification of 10 fold serial dilutions of HIV-1, Group M, subtype D RNA according to the preferred embodiment of the invention.
Figure 3:
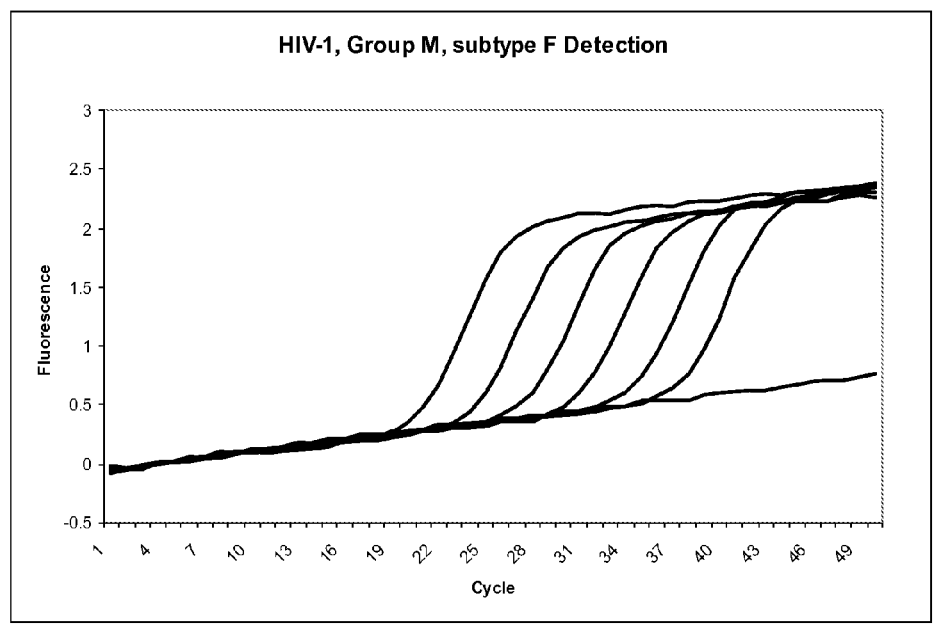
FIG. 3 depicts RT-PCR amplification of 10 fold serial dilutions of HIV-1, Group M, subtype F RNA according to the preferred embodiment of the invention.
Figure 4:
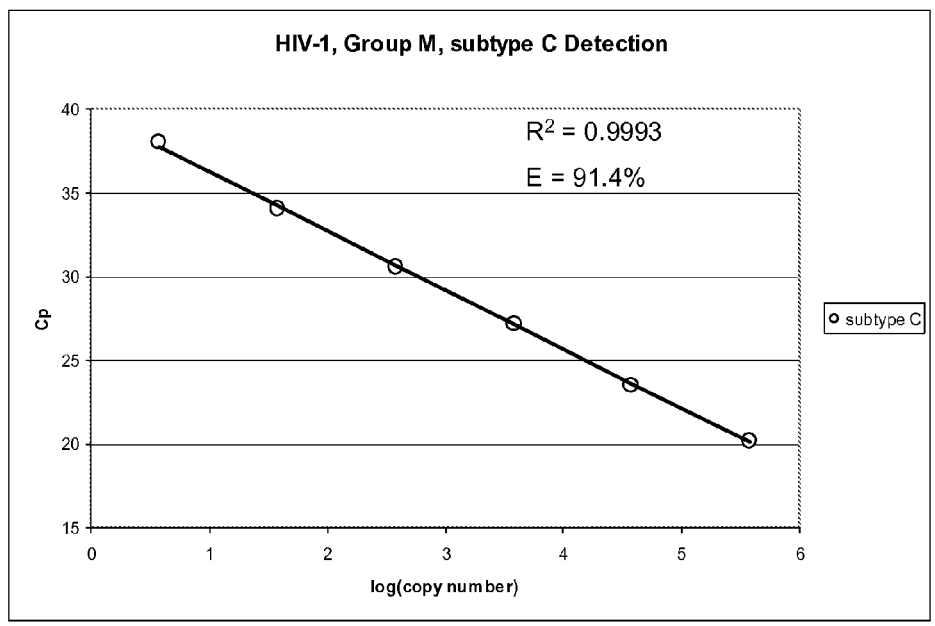
FIG. 4 depicts the graph plotting Cp values versus the copy number of template for the RT-PCR reactions of HIV-1, Group M, subtype C detection.
Figure 5:
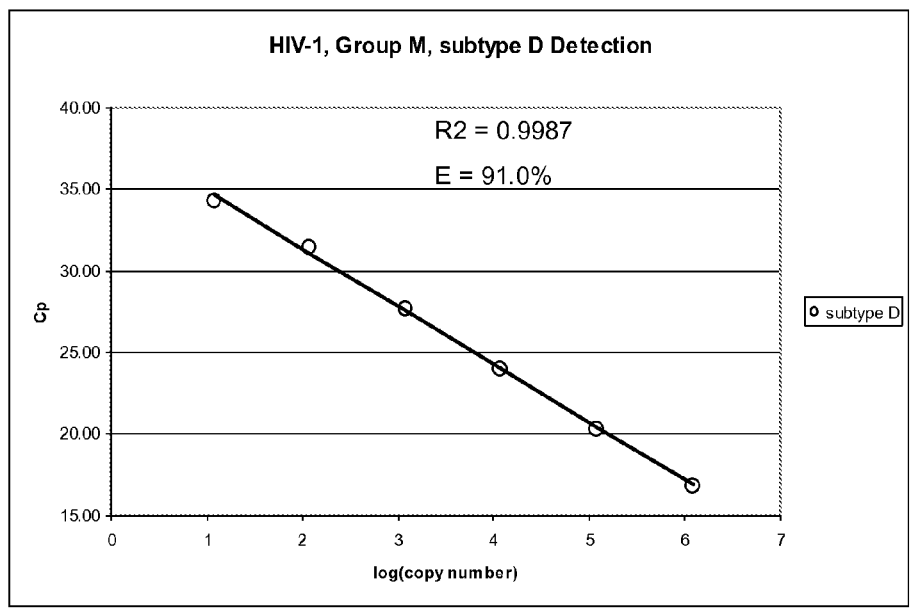
FIG. 5 depicts the graph plotting Cp values versus the copy number of template for the RT-PCR reactions of HIV-1, Group M, subtype D detection.
Figure 6:
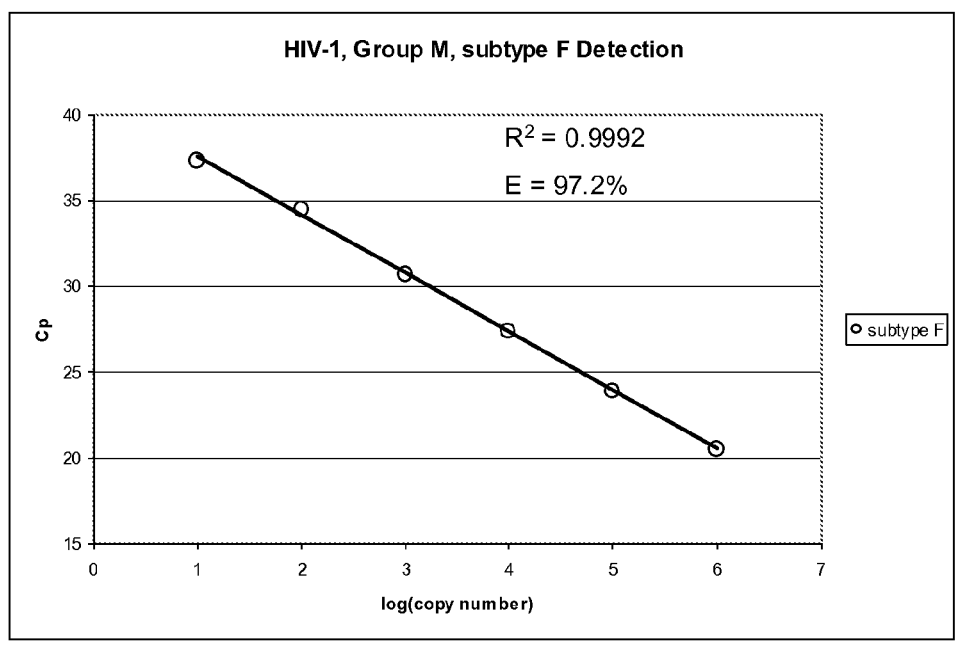
FIG. 6 depicts the graph plotting Cp values versus the copy number of template for the RT-PCR reactions of HIV-1, Group M, subtype F detection.

The RT-PCR examples shown in FIGS. 1-3 were performed using RNA template derived from HIV-1, Group M, subtype C, subtype D and subtype F respectively. These results demonstrate detection of multiple subtypes of HIV-1 when 11 or fewer copies of genomic RNA was used as template. FIGS. 4-6 show graphs that plot the Cp value of the amplification curve for each RNA dilution versus the log (copy number) of template. Each plot demonstrates linearity for the reaction over 5 orders of magnitude for each sample with $r^2$ values of greater than 0.99 representing good linear fit for the data. The efficiencies for these reactions were 91% for subtype C, 91% for subtype D and 97% for subtype F. Table 2 shows a list of HIV-1 strains that were tested in this study and the lower limit of detection for each strain. These results demonstrate inclusivity across all subtypes of HIV-1 Group M that were tested.

Example 2

Method of Detecting HIV-1 Group O

RNA templates used for detection of HIV-1 Group O were purchased from Seracare Life Sciences and are listed in Table 2. Ten fold serial dilutions of RNA template were prepared in 5 mM HEPES (4-(2-hydroxyethyl)-1-(piperazineethanesulfonic acid)-KOH, pH 7.8) such that the sample of greatest dilution contained between 1 and 11 copies of RNA template. 1 μl of each dilution was used as RNA template in a one-step RT-PCR reaction with 24 μl of PCR mix. The final concentrations of each component in the RT-PCR reaction were as follows, 1× PCR reaction buffer, 300 nM forward primer (SEQ ID NO: 1), 300 nM reverse primer (SEQ ID NO: 14), 200 nM CATACLEAVE™ probe (SEQ ID: 22), 5 u "Hot Start" RNase HII, 2 u Platinum TAQ™ DNA Polymerase (Life Technologies) and 0.5 u SUPERSCRIPT™ III reverse transcriptase (Life Technologies). The one-step RT-PCR reactions were performed on a LightCycler LIGHTCYCLER™ 480 real-time PCR machine (Roche) using the following cycling parameters, 50° C. for 15 min for first strand cDNA synthesis, 95° C. for 5 min to heat inactivate the reverse transcriptase and heat activate the RNase HII and DNA polymerase followed by 50 cycles of denaturation at 95° C. for 10 sec, annealing at 55° C. for 10 sec and elongation at 72° C. for 30 sec. Fluorescence readings were taken at each cycle during the 72° C. elongation step.

Figure 8:
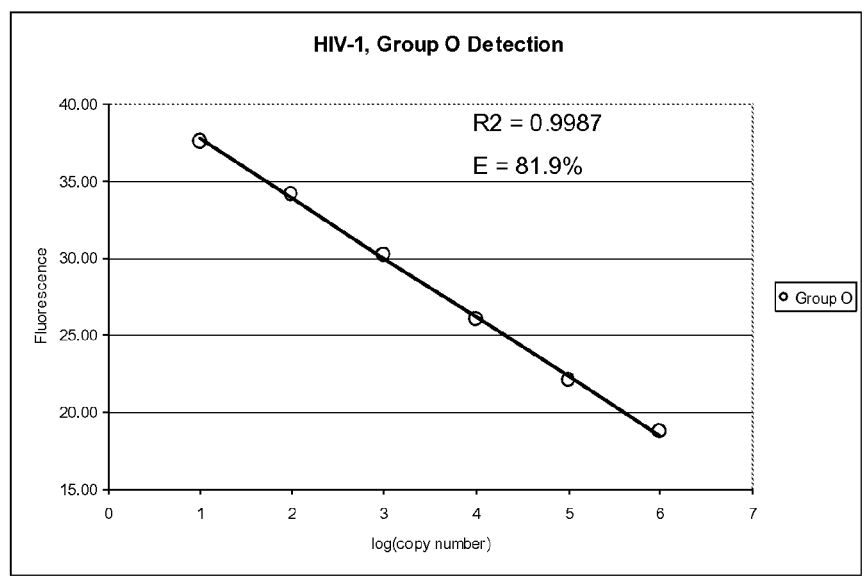
FIG. 8 depicts the graph plotting Cp values versus the copy number of template for the RT-PCR reactions of HIV-1, Group O.

The RT-PCR example shown in FIG. 7 was performed using RNA template derived from HIV-1, Group O, strain 1-2481. Table 2 shows a list of HIV-1 Group O strains that were tested and the lower limit of detection for the assay. These results demonstrate detection of multiple strains of HIV-1 Group O when 11 or fewer copies of genomic RNA were used as template. FIG. 8 shows a graph that plots the Cp value of the amplification curve for each RNA dilution versus the log (copy number) of template. The plot demonstrates linearity for the reaction over 5 orders of magnitude with an $r^2$ value of greater than 0.99 representing good linear fit for the data. The efficiency of the reaction detecting 1-2481 was 82%. Table 2 shows a list of HIV-1 Group O strains that were tested and the lower limit of detection for the assay. These results demonstrate inclusivity across all HIV-1 Group O strains that were tested.

TABLE 1

| SEQ ID NO: | Primer/Probe | Sequence (5'-3') |
|---|---|---|
| 1 | HIV-Pol-F3 | GCAGTACAAATGGCAGTATTCATCCACAATT |
| 2 | HIV-Pol-F7 | CAGCAGTACAAATGGCAGTATTCATCCA |
| 3 | HIV-Pol-N-F42 | CAGGAATTCGGGATACCCTACAATCCTCAA |
| 4 | HIV-Pol-N-F43 | AGGAATTCGGGATACCCTACAATCCTCAAA |
| 5 | HIV-Pol-N-F58 | ACAATCCTCAAAGTCAGGGAGTAGTAGAAT |
| 6 | HIV-Pol-N-F66 | CAAAGTCAGGGAGTAGTAGAATCCATGAAT |
| 7 | HIV-1_F10-JO | CCAAGGGGAAGTGACATAGCAGGAACTACTA |
| 8 | HIV-1_F11-JO | CCAAGGGGAAGTGACATAGCAGGAACTACT |
| 9 | HIV-1_R6-JO | CTGACAGGGCTATACATTCTTACTATTTTATT |

TABLE 1-continued

| SEQ ID NO: | Primer/Probe | Sequence (5'-3') |
|---|---|---|
| 10 | HIV-Pol-R9 | TTTCTGCTGTCCCTGTAATAAACCCGAAAATTT |
| 11 | HIV-Pol-R21 | TCTCTGCTGTCCCTGTAATAAACCCGAAAATTT |
| 12 | HIV-Pol-R22 | CTCTGCTGTCCCTGTAATAAACCCGAAAATTT |
| 13 | HIV-Pol-R23 | TCTGCTGTCCCTGTAATAAACCCGAAAATTT |
| 14 | HIV-Pol-R26_O | CTCTGCTGTCTCTGTAATAGACCCGAAAATTT |
| 15 | HIV-Pol-R27_O | CTCTGCTGTCTCTGTAATAGACCCGAAAATT |
| 16 | HIV-Pol-R28_O | CTCTGCTGTCTCTGTAATAGACCCGAAAATTTT |
| 17 | HIV-Pol-O-R39 | GTCCTTTCCAAATAGGATCTCTGCTATCTC |
| 18 | HIV-Pol-O-R46 | CCAAATAGGATCTCTGCTATCTCTGTAATA |
| 19 | HIV-Pol-O-R47 | AAATAGGATCTCTGCTATCTCTGTAATAGA |
| 20 | HIV-1_CCProbe5 | FAM/TACCCTTCAGrGrArArCAAATAGGATGGAT/IABkFQ |
| 21 | HIV-1_CCProbe8 | FAM/GGAGAAATTTATAArArArGrATGGATAATCCTGG/IABkFQ |
| 22 | HIV-1_CCProbe24 | FAM/TTAAAAGAAAAGGGGrGrGrArUTGGGGGGTACA/IABkFQ |
| 23 | HIV-1_CCProbe25 | FAM/TTAAAAGAAAAGGGGrGrGrArUrUGGGGGGTACA/IABkFQ |
| 24 | HIV-1_CCProbe27 | FAM/TGTACCCCCArArUrCrCCCCCTTTTCTTTTAA/IABkFQ |
| 25 | HIV-1_CCProbe28 | FAM/TTAAAAGAAAGG*GG*rGrGrArUTG*GG*GG*GTACA/EDQ |
| 26 | HIV-1_FPX | $X_1AGX_2AX_3TX_4CAX_5ATGGCAGTX_6X_7TX_8ATX_9CAX_{10}AATT$ |
| 27 | HIV-1_FPX2 | $CAGGAX_1TTX_2GGGATACCX_3TACAATCCTCAAAGTCAGGGAGX_4X_5GTAGAX_6TCCATGAAT$ |
| 28 | HIV-1_FPX3 | $CCX_1X_2X_3X_4GX_5X_6X_7GX_8GX_9X_{10}X_{11}TAX_{12}CAGGX_{13}X_{14}X_{15}X_{16}X_{17}CTA$ |
| 29 | HIV-1_RPX | $CX_1X_2X_3X_4X_5GX_6X_7X_8X_9X_{10}X_{11}ACAX_{12}X_{13}CX_{14}X_{15}ACTATX_{16}X_{17}X_{18}X_{19}TX_{20}$ |
| 30 | HIV-1_RPX2 | $TX_1TX_2TGX_3TX_4TCX_5CX_6GX_7AAX_8AX_9X_{10}CCX_{11}GX_{12}AAATX_{13}X_{14}X_{15}$ |
| 31 | HIV-1_RPX3 | $X_1X_2CCTTX_3CCAX_4X_5X_6X_7GGX_8TX_9TX_{10}TGX_{11}TX_{12}TCX_{13}CTGX_{14}AAX_{15}AX_{16}X_{17}$ |

In the above Table 1, probes of SEQ ID NOS: 20-25 are shown as having a detectable label at each of 5' and 3' ends thereof, and the nucleotides "rA," "rG," "rU, and "rC" are ribonucleotides and the nucleotide G* is 8-Aza-7-Deaza-dG.

Further, for SEQ ID NO: 26, $X_1$ is C or G $X_2$ is C or T, $X_3$ is G or T, $X_4$ is A or G, $X_5$ is A or G, $X_6$ is A or G or T, $X_7$ is T or C, $X_8$ is T or C, $X_9$ is T or C, and $X_{10}$ is T or C.

For SEQ ID NO: 27, $X_1$ is A or G, $X_2$ is C or T, $X_3$ is C or A, $X_4$ is C or T, $X_5$ is A or G, $X_6$ is A or G.

For SEQ ID NO: 28, $X_1$ is A or G or C or T, $X_2$ is A or G, $X_3$ is G or C or T, $X_4$ is A or G, $X_5$ is A or G or C, $X_6$ is T or A, $X_7$ is A or G, $X_8$ is T or G, $X_9$ is G or A or C, $X_{10}$ is C or T, $X_{11}$ is A or T, $X_{12}$ is G or C or C, $X_{13}$ is G or A, $X_{14}$ is A or G or T or C, $X_{15}$ is T or C or G, $X_{16}$ is T or C and $X_{17}$ is A or C.

For SEQ ID NO: 29, $X_1$ is A or T, $X_2$ is G or A, $X_3$ is C or A or G, $X_4$ is T or C or A, $X_5$ is A or T or G, $X_6$ is G or A, $X_7$ is A or G, $X_8$ is C or T, $X_9$ is T or G or A, $X_{10}$ is A or G, $X_{11}$ is T or A, $X_{12}$ is T or C, $X_{13}$ is T or C, $X_{14}$ is T or C, $X_{15}$ is T or C, $X_{16}$ is T or C, $X_{17}$ is T or A, $X_{18}$ is T or G, $X_{19}$ is A or G and $X_{20}$ is T or C.

For SEQ ID NO: 30, $X_1$ is C or T, $X_2$ is T or C, $X_3$ is C or T, $X_4$ is A or G, $X_5$ is T or C, $X_6$ is T or C, $X_7$ is A or T, $X_8$ is A or T, $X_9$ is G or A, $X_{10}$ is A or G, $X_{11}$ is T or C, $X_{12}$ is A or G, $X_{13}$ is A or T or G, $X_{14}$ is T or G, and $X_{15}$ is T or C or G.

For SEQ ID NO: 31, $X_1$ is G or A, $X_2$ is T or C, $X_3$ is C or T, $X_4$ is A or G, $X_5$ is A or G, $X_6$ is T or C or G, $X_7$ is A or T or C or G, $X_8$ is A or G, $X_9$ is C or T, $X_{10}$ is C or T, $X_{11}$ is C or T, $X_{12}$ is C or A, $X_{13}$ is C or T, $X_{14}$ is T or A, $X_{15}$ is T or A, $X_{16}$ is A or G and $X_{17}$ is A or G.

TABLE 2

| Virus | Group | Subtype | Isolate Name | Starting Concentration (copies) | Limit of Detection (Copies) |
|---|---|---|---|---|---|
| HIV-1 | M | A | I-2496 | 1.84E+05 | 2 |
| HIV-1 | M | B | BK132 | 1.14E+06 | 11 |
| HIV-1 | M | C | DJ259 | 3.83E+05 | 4 |
| HIV-1 | M | D | SE365 | 6.46E+05 | 6 |
| HIV-1 | M | D | UG274 | 1.23E+06 | 12 |
| HIV-1 | M | A/E | 42368 | 1.96E+06 | 19 |
| HIV-1 | M | F | BZ126 | 2.76E+06 | 3 |
| HIV-1 | M | F | BZ162 | 9.98E+05 | 10 |
| HIV-1 | M | A/G | POC44951 | 4.66E+06 | 5 |
| HIV-1 | M | G | HH8793 | 5.74E+05 | 57 |
| HIV-1 | M | H | BCF-KITA | 6.50E+05 | 65 |
| HIV-1 | O | | I-2481 | 1.1E+06 | 11 |
| HIV-1 | O | | BCF06 | 7.7E+05 | 8 |
| HIV-1 | O | | BCF11 | 5.8E+05 | 6 |

TABLE 2-continued

| Virus | Group | Subtype | Isolate Name | Starting Concentration (copies) | Limit of Detection (Copies) |
|---|---|---|---|---|---|

Other exemplary combinations of the forward and reverse primers and probes are shown n Table 3.

TABLE 3

| Primer Pairs (SEQ ID NO) | | Probes |
|---|---|---|
| Forward Primer | Reverse Primer | (SEQ ID NOS) |
| 1 | 10, 11, 12, 13, 14, 15, 16, 17, 18, 19 | 22, 23, 24, 25 |
| 2 | 10, 11, 12, 13, 14, 15, 16, 17, 18, 19 | 22, 23, 24, 25 |
| 3 | 10, 11, 12, 13, 14, 15, 16, 17, 18, 19 | 22, 23, 24, 25 |

TABLE 3-continued

| Primer Pairs (SEQ ID NO) | | Probes |
|---|---|---|
| Forward Primer | Reverse Primer | (SEQ ID NOS) |
| 4 | 10, 11, 12, 13, 14, 15, 16, 17, 18, 19 | 22, 23, 24, 25 |
| 5 | 10, 11, 12, 13, 14, 15, 16, 17, 18, 19 | 22, 23, 24, 25 |
| 6 | 10, 11, 12, 13, 14, 15, 16, 17, 18, 19 | 22, 23, 24, 25 |
| 7 | 9 | 20, 21 |
| 8 | 9 | 20, 21 |

Any patent, patent application, publication, or other disclosure material identified in the specification is hereby incorporated by reference herein in its entirety. Any material, or portion thereof, that is said to be incorporated by reference herein, but which conflicts with existing definitions, statements, or other disclosure material set forth herein is only incorporated to the extent that no conflict arises between that incorporated material and the present disclosure material.

What is claimed is:

1. A kit for detecting HIV-1, comprising:

a first primer comprising the oligonucleotide of the nucleotide sequence selected from the group consisting of SEQ ID NO: 1, 2, 3, 4, 5, 6, 7, and 8:

```
                                          (SEQ ID NO: 1)
GCAGTACAAATGGCAGTATTCATCCACAATT, (SEQ ID NO: 2)
CAGCAGTACAAATGGCAGTATTCATCCA, (SEQ ID NO: 3)
CAGGAATTCGGGATACCCTACAATCCTCAA, (SEQ ID NO: 4)
AGGAATTCGGGATACCCTACAATCCTCAAA, (SEQ ID NO: 5)
ACAATCCTCAAAGTCAGGGAGTAGTAGAAT, (SEQ ID NO: 6)
CAAAGTCAGGGAGTAGTAGAATCCATGAAT, (SEQ ID NO: 7)
CCAAGGGGAAGTGACATAGCAGGAACTACTA,
and (SEQ ID NO: 8)
CCAAGGGGAAGTGACATAGCAGGAACTACT.
``` a second primer comprising the oligonucleotide of the nucleotide sequence selected from the group consisting of SEQ ID NO: 9, 10, 11, 12, 13, 14, 15, 16, 17, 18 and 19:

```
                                          (SEQ ID NO: 9)
CTGACAGGGCTATACATTCTTACTATTTTATT, (SEQ ID NO: 10)
TTTCTGCTGTCCCTGTAATAAACCCGAAAATTT, (SEQ ID NO: 11)
TCTCTGCTGTCCCTGTAATAAACCCGAAAATTT, (SEQ ID NO: 12)
CTCTGCTGTCCCTGTAATAAACCCGAAAATTT, (SEQ ID NO: 13)
TCTGCTGTCCCTGTAATAAACCCGAAAATTT, (SEQ ID NO: 14)
CTCTGCTGTCTCTGTAATAGACCCGAAAATTT, (SEQ ID NO: 15)
CTCTGCTGTCTCTGTAATAGACCCGAAAATT, (SEQ ID NO: 16)
CTCTGCTGTCTCTGTAATAGACCCGAAAATTTT, (SEQ ID NO: 17)
GTCCTTTCCAAATAGGATCTCTGCTATCTC, (SEQ ID NO: 18)
CCAAATAGGATCTCTGCTATCTCTGTAATA,
and (SEQ ID NO: 19)
AAATAGGATCTCTGCTATCTCTGTAATAGA,
``` and a probe comprising the oligonucleotide of the nucleotide sequence selected from the group consisting of SEQ ID NO: 20, 21, 22, 23, 24 and 25:

```
                                          (SEQ ID NO: 20)
TACCCTTCAGrGrArArCAAATAGGATGGAT, (SEQ ID NO: 21)
GGAGAAATTTATAArArArGrATGGATAATCCTG, (SEQ ID NO: 22)
TTAAAAGAAAAGGGGrGrGrArUTGGGGGGTACA, (SEQ ID NO: 23)
TTAAAAGAAAAGGGGrGrArUrUGGGGGGTACA, (SEQ ID NO: 24)
TGTACCCCCArArUrCrCCCCCTTTTCTTTTAA,
and (SEQ ID NO: 25)
TTAAAAGAAAAGG*GG*rGrGrArUTG*GG*GG*GTACA,
``` wherein the nucleotides "rA," "rG," "rU, and "rC" are ribonucleotides and the nucleotide G* is 8-Aza-7-Deaza-dG.

2. The kit of claim 1, which further comprises an amplifying polymerase activity and an RNase H activity.

3. The kit of claim 1, which further comprises a reverse transcriptase activity.

4. The kit of claim 1, wherein a 5' end of each probe is labeled with a fluorescence label or a 3' end of each of the probes is labeled with a fluorescence quencher.

5. The kit of claim 1, further comprising a mixture comprising dATP, dCTP, dGTP, and dTTP; a DNA polymerase; RNase HII; and a buffer solution.

6. The kit of claim 1, further comprising uracil-N-glycosylase.

7. The kit of claim 1, wherein the probe is linked to a solid support.

8. The kit of claim 1, wherein the probe is present as a free form in a solution.

9. The kit of claim 2, wherein the amplifying polymerase activity is the activity of a thermostable DNA polymerase.

10. The kit of claim 2, wherein the RNase H activity is the activity of a thermostable RNase H.

11. The kit of claim 2, wherein the RNase H activity is a hot start RNase H activity.

* * * * *

```
                        SEQUENCE LISTING

<160> NUMBER OF SEQ ID NOS: 31

<210> SEQ ID NO 1
<211> LENGTH: 31
<212> TYPE: DNA
<213> ORGANISM: Artificial Sequence
<220> FEATURE:
<223> OTHER INFORMATION: Forward Primer (HIV-Pol-F3)

<400> SEQUENCE: 1
gcagtacaaa tggcagtatt catccacaat t                                    31

<210> SEQ ID NO 2
<211> LENGTH: 28
<212> TYPE: DNA
<213> ORGANISM: Artificial Sequence
<220> FEATURE:
<223> OTHER INFORMATION: Forward Primer (HIV-Pol-F7)

<400> SEQUENCE: 2
cagcagtaca aatggcagta ttcatcca                                        28

<210> SEQ ID NO 3
<211> LENGTH: 30
<212> TYPE: DNA
<213> ORGANISM: Artificial Sequence
<220> FEATURE:
<223> OTHER INFORMATION: Forward Primer (HIV-Pol-N-F42)

<400> SEQUENCE: 3
caggaattcg ggatacccta caatcctcaa                                      30

<210> SEQ ID NO 4
<211> LENGTH: 30
<212> TYPE: DNA
<213> ORGANISM: Artificial Sequence
<220> FEATURE:
<223> OTHER INFORMATION: Forward Primer (HIV-Pol-N-F43)

<400> SEQUENCE: 4
aggaattcgg gatacccctac aatcctcaaa                                     30

<210> SEQ ID NO 5
<211> LENGTH: 30
<212> TYPE: DNA
```

```
<213> ORGANISM: Artificial Sequence
<220> FEATURE:
<223> OTHER INFORMATION: Forward Primer (HIV-Pol-N-F58)

<400> SEQUENCE: 5
acaatcctca aagtcaggga gtagtagaat                                    30

<210> SEQ ID NO 6
<211> LENGTH: 30
<212> TYPE: DNA
<213> ORGANISM: Artificial Sequence
<220> FEATURE:
<223> OTHER INFORMATION: Forward Primer (HIV-Pol-N-F66)

<400> SEQUENCE: 6
caaagtcagg gagtagtaga atccatgaat                                    30

<210> SEQ ID NO 7
<211> LENGTH: 31
<212> TYPE: DNA
<213> ORGANISM: Artificial Sequence
<220> FEATURE:
<223> OTHER INFORMATION: Forward Primer (HIV-1_F10-JO)

<400> SEQUENCE: 7
ccaaggggaa gtgacatagc aggaactact a                                  31

<210> SEQ ID NO 8
<211> LENGTH: 30
<212> TYPE: DNA
<213> ORGANISM: Artificial Sequence
<220> FEATURE:
<223> OTHER INFORMATION: Forward Primer (HIV-1_F11-JO)

<400> SEQUENCE: 8
ccaaggggaa gtgacatagc aggaactact                                    30

<210> SEQ ID NO 9
<211> LENGTH: 32
<212> TYPE: DNA
<213> ORGANISM: Artificial Sequence
<220> FEATURE:
<223> OTHER INFORMATION: Reverse Primer (HIV-1_R6-JO)

<400> SEQUENCE: 9
ctgacagggc tatacattct tactatttta tt                                 32

<210> SEQ ID NO 10
<211> LENGTH: 33
<212> TYPE: DNA
<213> ORGANISM: Artificial Sequence
<220> FEATURE:
<223> OTHER INFORMATION: Reverse Primer (HIV-Pol-R9)

<400> SEQUENCE: 10
tttctgctgt ccctgtaata aacccgaaaa ttt                                33

<210> SEQ ID NO 11
<211> LENGTH: 33
<212> TYPE: DNA
<213> ORGANISM: Artificial Sequence
<220> FEATURE:
<223> OTHER INFORMATION: Reverse Primer (HIV-Pol-R21)

<400> SEQUENCE: 11
tctctgctgt ccctgtaata aacccgaaaa ttt                                33
```

<210> SEQ ID NO 12
<211> LENGTH: 32
<212> TYPE: DNA
<213> ORGANISM: Artificial Sequence
<220> FEATURE:
<223> OTHER INFORMATION: Reverse Primer (HIV-Pol-R22)

<400> SEQUENCE: 12
ctctgctgtc cctgtaataa acccgaaaat tt                                32

<210> SEQ ID NO 13
<211> LENGTH: 31
<212> TYPE: DNA
<213> ORGANISM: Artificial Sequence
<220> FEATURE:
<223> OTHER INFORMATION: Reverse Primer (HIV-Pol-R23)

<400> SEQUENCE: 13
tctgctgtcc ctgtaataaa cccgaaaatt t                                 31

<210> SEQ ID NO 14
<211> LENGTH: 32
<212> TYPE: DNA
<213> ORGANISM: Artificial Sequence
<220> FEATURE:
<223> OTHER INFORMATION: Reverse Primer (HIV-Pol-R26_O)

<400> SEQUENCE: 14
ctctgctgtc tctgtaatag acccgaaaat tt                                32

<210> SEQ ID NO 15
<211> LENGTH: 31
<212> TYPE: DNA
<213> ORGANISM: Artificial Sequence
<220> FEATURE:
<223> OTHER INFORMATION: Reverse Primer (HIV-Pol-R27_O)

<400> SEQUENCE: 15
ctctgctgtc tctgtaatag acccgaaaat t                                 31

<210> SEQ ID NO 16
<211> LENGTH: 33
<212> TYPE: DNA
<213> ORGANISM: Artificial Sequence
<220> FEATURE:
<223> OTHER INFORMATION: Reverse Primer (HIV-Pol-R28_O)

<400> SEQUENCE: 16
ctctgctgtc tctgtaatag acccgaaaat ttt                               33

<210> SEQ ID NO 17
<211> LENGTH: 30
<212> TYPE: DNA
<213> ORGANISM: Artificial Sequence
<220> FEATURE:
<223> OTHER INFORMATION: Reverse Primer (HIV-Pol-O-R39)

<400> SEQUENCE: 17
gtcctttcca aataggatct ctgctatctc                                   30

<210> SEQ ID NO 18
<211> LENGTH: 30
<212> TYPE: DNA
<213> ORGANISM: Artificial Sequence
<220> FEATURE:

<223> OTHER INFORMATION: Reverse Primer (HIV-Pol-O-R46)

<400> SEQUENCE: 18
ccaaatagga tctctgctat ctctgtaata                             30

<210> SEQ ID NO 19
<211> LENGTH: 30
<212> TYPE: DNA
<213> ORGANISM: Artificial Sequence
<220> FEATURE:
<223> OTHER INFORMATION: Reverse Primer (HIV-Pol-O-R47)

<400> SEQUENCE: 19
aaataggatc tctgctatct ctgtaataga                             30

<210> SEQ ID NO 20
<211> LENGTH: 27
<212> TYPE: DNA
<213> ORGANISM: Artificial Sequence
<220> FEATURE:
<223> OTHER INFORMATION: Synthetic Probe Construct
<220> FEATURE:
<221> NAME/KEY: misc_feature
<222> LOCATION: (11)..(14)
<223> OTHER INFORMATION: RNA Region

<400> SEQUENCE: 20 taccccttcag gaacaaatag gatggat                                27

<210> SEQ ID NO 21
<211> LENGTH: 31
<212> TYPE: DNA
<213> ORGANISM: Artificial Sequence
<220> FEATURE:
<223> OTHER INFORMATION: Synthetic Probe Construct
<220> FEATURE:
<221> NAME/KEY: misc_feature
<222> LOCATION: (15)..(18)
<223> OTHER INFORMATION: RNA Region

<400> SEQUENCE: 21
ggagaaattt ataaaagatg gataatcctg g                           31

<210> SEQ ID NO 22
<211> LENGTH: 30
<212> TYPE: DNA
<213> ORGANISM: Artificial Sequence
<220> FEATURE:
<223> OTHER INFORMATION: Synthetic Probe Construct
<220> FEATURE:
<221> NAME/KEY: misc_feature
<222> LOCATION: (16)..(19)
<223> OTHER INFORMATION: RNA Region

<400> SEQUENCE: 22
ttaaaagaaa aggggggaut gggggggtaca                            30

<210> SEQ ID NO 23
<211> LENGTH: 30
<212> TYPE: DNA
<213> ORGANISM: Artificial Sequence
<220> FEATURE:
<223> OTHER INFORMATION: Synthetic Probe Construct
<220> FEATURE:
<221> NAME/KEY: misc_feature
<222> LOCATION: (17)..(20)
<223> OTHER INFORMATION: RNA Region

<400> SEQUENCE: 23
ttaaaagaaa aggggggauu gggggggtaca					30

<210> SEQ ID NO 24
<211> LENGTH: 30
<212> TYPE: DNA
<213> ORGANISM: Artificial Sequence
<220> FEATURE:
<223> OTHER INFORMATION: Synthetic Probe Construct
<220> FEATURE:
<221> NAME/KEY: misc_feature
<222> LOCATION: (12)..(15)
<223> OTHER INFORMATION: RNA Region

<400> SEQUENCE: 24 tgtaccccc aaucccccct tttcttttaa					30

<210> SEQ ID NO 25
<211> LENGTH: 30
<212> TYPE: DNA
<213> ORGANISM: Artificial Sequence
<220> FEATURE:
<223> OTHER INFORMATION: Synthetic Probe Construct
<220> FEATURE:
<221> NAME/KEY: misc_feature
<222> LOCATION: (13)..(13)
<223> OTHER INFORMATION: 8-Aza-7-Deaza-dG
<220> FEATURE:
<221> NAME/KEY: misc_feature
<222> LOCATION: (16)..(19)
<223> OTHER INFORMATION: RNA Region
<220> FEATURE:
<221> NAME/KEY: misc_feature
<222> LOCATION: (15)..(15)
<223> OTHER INFORMATION: 8-Aza-7-Deaza-dG
<220> FEATURE:
<221> NAME/KEY: misc_feature
<222> LOCATION: (21)..(21)
<223> OTHER INFORMATION: 8-Aza-7-Deaza-dG
<220> FEATURE:
<221> NAME/KEY: misc_feature
<222> LOCATION: (23)..(23)
<223> OTHER INFORMATION: 8-Aza-7-Deaza-dG
<220> FEATURE:
<221> NAME/KEY: misc_feature
<222> LOCATION: (25)..(25)
<223> OTHER INFORMATION: 8-Aza-7-Deaza-dG

<400> SEQUENCE: 25
ttaaaagaaa aggggggaut gggggtaca					30

<210> SEQ ID NO 26
<211> LENGTH: 33
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: C or G
<220> FEATURE:
<221> NAME/KEY: misc_feature
<222> LOCATION: (4)..(4)
<223> OTHER INFORMATION: C or T
<220> FEATURE:
<221> NAME/KEY: misc_feature
<222> LOCATION: (6)..(6)
<223> OTHER INFORMATION: G or T
<220> FEATURE:
<221> NAME/KEY: misc_feature
<222> LOCATION: (8)..(8)
<223> OTHER INFORMATION: A or G
<220> FEATURE:

<221> NAME/KEY: misc_feature
<222> LOCATION: (11)..(11)
<223> OTHER INFORMATION: A or G
<220> FEATURE:
<221> NAME/KEY: misc_feature
<222> LOCATION: (20)..(20)
<223> OTHER INFORMATION: A or G or T
<220> FEATURE:
<221> NAME/KEY: misc_feature
<222> LOCATION: (21)..(21)
<223> OTHER INFORMATION: T or C
<220> FEATURE:
<221> NAME/KEY: misc_feature
<222> LOCATION: (23)..(23)
<223> OTHER INFORMATION: T or C
<220> FEATURE:
<221> NAME/KEY: misc_feature
<222> LOCATION: (26)..(26)
<223> OTHER INFORMATION: T or C
<220> FEATURE:
<221> NAME/KEY: misc_feature
<222> LOCATION: (29)..(29)
<223> OTHER INFORMATION: T or C

<400> SEQUENCE: 26
nagnantnca natggcagtn ntnatncana att                               33

<210> SEQ ID NO 27
<211> LENGTH: 57
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(6)
<223> OTHER INFORMATION: A or G
<220> FEATURE:
<221> NAME/KEY: misc_feature
<222> LOCATION: (9)..(9)
<223> OTHER INFORMATION: C or T
<220> FEATURE:
<221> NAME/KEY: misc_feature
<222> LOCATION: (18)..(18)
<223> OTHER INFORMATION: C or A
<220> FEATURE:
<221> NAME/KEY: misc_feature
<222> LOCATION: (41)..(41)
<223> OTHER INFORMATION: C or T
<220> FEATURE:
<221> NAME/KEY: misc_feature
<222> LOCATION: (42)..(42)
<223> OTHER INFORMATION: A or G
<220> FEATURE:
<221> NAME/KEY: misc_feature
<222> LOCATION: (48)..(48)
<223> OTHER INFORMATION: A or G

<400> SEQUENCE: 27
cagganttng ggataccnta caatcctcaa agtcagggag nngtagantc catgaat       57

<210> SEQ ID NO 28
<211> LENGTH: 31
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: A or G or C or T
<220> FEATURE:
<221> NAME/KEY: misc_feature
<222> LOCATION: (4)..(4)
<223> OTHER INFORMATION: A or G

```
<220> FEATURE:
<221> NAME/KEY: misc_feature
<222> LOCATION: (5)..(5)
<223> OTHER INFORMATION: G or C or T
<220> FEATURE:
<221> NAME/KEY: misc_feature
<222> LOCATION: (6)..(6)
<223> OTHER INFORMATION: A or G
<220> FEATURE:
<221> NAME/KEY: misc_feature
<222> LOCATION: (8)..(8)
<223> OTHER INFORMATION: A or G or C
<220> FEATURE:
<221> NAME/KEY: misc_feature
<222> LOCATION: (9)..(9)
<223> OTHER INFORMATION: T or A
<220> FEATURE:
<221> NAME/KEY: misc_feature
<222> LOCATION: (10)..(10)
<223> OTHER INFORMATION: A or G
<220> FEATURE:
<221> NAME/KEY: misc_feature
<222> LOCATION: (12)..(12)
<223> OTHER INFORMATION: T or G
<220> FEATURE:
<221> NAME/KEY: misc_feature
<222> LOCATION: (14)..(14)
<223> OTHER INFORMATION: G or A or C
<220> FEATURE:
<221> NAME/KEY: misc_feature
<222> LOCATION: (15)..(15)
<223> OTHER INFORMATION: C or T
<220> FEATURE:
<221> NAME/KEY: misc_feature
<222> LOCATION: (16)..(16)
<223> OTHER INFORMATION: A or T
<220> FEATURE:
<221> NAME/KEY: misc_feature
<222> LOCATION: (19)..(19)
<223> OTHER INFORMATION: G or C
<220> FEATURE:
<221> NAME/KEY: misc_feature
<222> LOCATION: (24)..(24)
<223> OTHER INFORMATION: G or A
<220> FEATURE:
<221> NAME/KEY: misc_feature
<222> LOCATION: (25)..(25)
<223> OTHER INFORMATION: A or G or T or C
<220> FEATURE:
<221> NAME/KEY: misc_feature
<222> LOCATION: (26)..(26)
<223> OTHER INFORMATION: T or C or G
<220> FEATURE:
<221> NAME/KEY: misc_feature
<222> LOCATION: (27)..(27)
<223> OTHER INFORMATION: T or C
<220> FEATURE:
<221> NAME/KEY: misc_feature
<222> LOCATION: (28)..(28)
<223> OTHER INFORMATION: A or C

<400> SEQUENCE: 28
ccnnnngnnn gngnnntanc aggnnnnnct a                                      31

<210> SEQ ID NO 29
<211> LENGTH: 32
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: A or T
<220> FEATURE:
<221> NAME/KEY: misc_feature
<222> LOCATION: (3)..(3)
```

```
<223> OTHER INFORMATION: G or A
<220> FEATURE:
<221> NAME/KEY: misc_feature
<222> LOCATION: (4)..(4)
<223> OTHER INFORMATION: C or A or G
<220> FEATURE:
<221> NAME/KEY: misc_feature
<222> LOCATION: (5)..(5)
<223> OTHER INFORMATION: T or C or A
<220> FEATURE:
<221> NAME/KEY: misc_feature
<222> LOCATION: (6)..(6)
<223> OTHER INFORMATION: A or T or G
<220> FEATURE:
<221> NAME/KEY: misc_feature
<222> LOCATION: (8)..(8)
<223> OTHER INFORMATION: G or A
<220> FEATURE:
<221> NAME/KEY: misc_feature
<222> LOCATION: (9)..(9)
<223> OTHER INFORMATION: A or G
<220> FEATURE:
<221> NAME/KEY: misc_feature
<222> LOCATION: (10)..(10)
<223> OTHER INFORMATION: C or T
<220> FEATURE:
<221> NAME/KEY: misc_feature
<222> LOCATION: (11)..(11)
<223> OTHER INFORMATION: T or G or A
<220> FEATURE:
<221> NAME/KEY: misc_feature
<222> LOCATION: (12)..(12)
<223> OTHER INFORMATION: A or G
<220> FEATURE:
<221> NAME/KEY: misc_feature
<222> LOCATION: (13)..(13)
<223> OTHER INFORMATION: T or A
<220> FEATURE:
<221> NAME/KEY: misc_feature
<222> LOCATION: (17)..(17)
<223> OTHER INFORMATION: T or C
<220> FEATURE:
<221> NAME/KEY: misc_feature
<222> LOCATION: (18)..(18)
<223> OTHER INFORMATION: T or C
<220> FEATURE:
<221> NAME/KEY: misc_feature
<222> LOCATION: (20)..(20)
<223> OTHER INFORMATION: T or C
<220> FEATURE:
<221> NAME/KEY: misc_feature
<222> LOCATION: (21)..(21)
<223> OTHER INFORMATION: T or C
<220> FEATURE:
<221> NAME/KEY: misc_feature
<222> LOCATION: (27)..(27)
<223> OTHER INFORMATION: T or C
<220> FEATURE:
<221> NAME/KEY: misc_feature
<222> LOCATION: (28)..(28)
<223> OTHER INFORMATION: T or A
<220> FEATURE:
<221> NAME/KEY: misc_feature
<222> LOCATION: (29)..(29)
<223> OTHER INFORMATION: T or G
<220> FEATURE:
<221> NAME/KEY: misc_feature
<222> LOCATION: (30)..(30)
<223> OTHER INFORMATION: A or G
<220> FEATURE:
<221> NAME/KEY: misc_feature
<222> LOCATION: (32)..(32)
<223> OTHER INFORMATION: T or C

<400> SEQUENCE: 29
cnnnnngnnn nnnacanncn nactatnnnn tn                                  32
```

-continued

```
<210> SEQ ID NO 30
<211> LENGTH: 34
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: C or T
<220> FEATURE:
<221> NAME/KEY: misc_feature
<222> LOCATION: (4)..(4)
<223> OTHER INFORMATION: C or T
<220> FEATURE:
<221> NAME/KEY: misc_feature
<222> LOCATION: (7)..(7)
<223> OTHER INFORMATION: C or T
<220> FEATURE:
<221> NAME/KEY: misc_feature
<222> LOCATION: (9)..(9)
<223> OTHER INFORMATION: A or G
<220> FEATURE:
<221> NAME/KEY: misc_feature
<222> LOCATION: (12)..(12)
<223> OTHER INFORMATION: T or C
<220> FEATURE:
<221> NAME/KEY: misc_feature
<222> LOCATION: (14)..(14)
<223> OTHER INFORMATION: T or C
<220> FEATURE:
<221> NAME/KEY: misc_feature
<222> LOCATION: (16)..(16)
<223> OTHER INFORMATION: A or T
<220> FEATURE:
<221> NAME/KEY: misc_feature
<222> LOCATION: (19)..(19)
<223> OTHER INFORMATION: A or T
<220> FEATURE:
<221> NAME/KEY: misc_feature
<222> LOCATION: (21)..(21)
<223> OTHER INFORMATION: G or A
<220> FEATURE:
<221> NAME/KEY: misc_feature
<222> LOCATION: (22)..(22)
<223> OTHER INFORMATION: A or G
<220> FEATURE:
<221> NAME/KEY: misc_feature
<222> LOCATION: (25)..(25)
<223> OTHER INFORMATION: T or C
<220> FEATURE:
<221> NAME/KEY: misc_feature
<222> LOCATION: (27)..(27)
<223> OTHER INFORMATION: A or G
<220> FEATURE:
<221> NAME/KEY: misc_feature
<222> LOCATION: (32)..(32)
<223> OTHER INFORMATION: A or T or G
<220> FEATURE:
<221> NAME/KEY: misc_feature
<222> LOCATION: (33)..(33)
<223> OTHER INFORMATION: T or G
<220> FEATURE:
<221> NAME/KEY: misc_feature
<222> LOCATION: (34)..(34)
<223> OTHER INFORMATION: T or C or G

<400> SEQUENCE: 30
tntntgntnt cncngnaana nnccngnaaa tnnn                                34

<210> SEQ ID NO 31
<211> LENGTH: 39
<212> TYPE: DNA
<213> ORGANISM: Artificial Sequence
<220> FEATURE:
<223> OTHER INFORMATION: Synthetic Construct
<220> FEATURE:
```

```
<221> NAME/KEY: misc_feature
<222> LOCATION: (1)..(1)
<223> OTHER INFORMATION: G or A
<220> FEATURE:
<221> NAME/KEY: misc_feature
<222> LOCATION: (2)..(2)
<223> OTHER INFORMATION: T or C
<220> FEATURE:
<221> NAME/KEY: misc_feature
<222> LOCATION: (7)..(7)
<223> OTHER INFORMATION: T or C
<220> FEATURE:
<221> NAME/KEY: misc_feature
<222> LOCATION: (9)..(9)
<223> OTHER INFORMATION: A or G
<220> FEATURE:
<221> NAME/KEY: misc_feature
<222> LOCATION: (11)..(11)
<223> OTHER INFORMATION: A or G
<220> FEATURE:
<221> NAME/KEY: misc_feature
<222> LOCATION: (12)..(12)
<223> OTHER INFORMATION: A or G
<220> FEATURE:
<221> NAME/KEY: misc_feature
<222> LOCATION: (13)..(13)
<223> OTHER INFORMATION: T or C or G
<220> FEATURE:
<221> NAME/KEY: misc_feature
<222> LOCATION: (14)..(14)
<223> OTHER INFORMATION: A or T or C or G
<220> FEATURE:
<221> NAME/KEY: misc_feature
<222> LOCATION: (17)..(17)
<223> OTHER INFORMATION: A or G
<220> FEATURE:
<221> NAME/KEY: misc_feature
<222> LOCATION: (19)..(19)
<223> OTHER INFORMATION: C or T
<220> FEATURE:
<221> NAME/KEY: misc_feature
<222> LOCATION: (21)..(21)
<223> OTHER INFORMATION: C or T
<220> FEATURE:
<221> NAME/KEY: misc_feature
<222> LOCATION: (24)..(24)
<223> OTHER INFORMATION: C or T
<220> FEATURE:
<221> NAME/KEY: misc_feature
<222> LOCATION: (26)..(26)
<223> OTHER INFORMATION: C or A
<220> FEATURE:
<221> NAME/KEY: misc_feature
<222> LOCATION: (29)..(29)
<223> OTHER INFORMATION: C or T
<220> FEATURE:
<221> NAME/KEY: misc_feature
<222> LOCATION: (33)..(33)
<223> OTHER INFORMATION: T or A
<220> FEATURE:
<221> NAME/KEY: misc_feature
<222> LOCATION: (36)..(36)
<223> OTHER INFORMATION: T or A
<220> FEATURE:
<221> NAME/KEY: misc_feature
<222> LOCATION: (38)..(38)
<223> OTHER INFORMATION: A or G
<220> FEATURE:
<221> NAME/KEY: misc_feature
<222> LOCATION: (39)..(39)
<223> OTHER INFORMATION: A or G

<400> SEQUENCE: 31
nnccttncca nnnnggntnt ntgntntcnc tgnaanann            39
```